United States Patent [19]
Bestwick et al.

[11] Patent Number: 6,118,049
[45] Date of Patent: Sep. 12, 2000

[54] SYNTHETIC HYBRID TOMATO E4/E8 PLANT PROMOTER

[75] Inventors: Richard K. Bestwick; Jill Anne Kellogg, both of Portland, Oreg.

[73] Assignee: Agritope, Inc., Portland, Oreg.

[21] Appl. No.: 09/157,077

[22] Filed: Sep. 18, 1998

Related U.S. Application Data

[60] Provisional application No. 60/059,234, Sep. 18, 1997.

[51] Int. Cl.⁷ .............................. C07H 21/04; C12N 5/14; C12N 15/82
[52] U.S. Cl. ...................... 800/283; 435/320.1; 435/419; 536/24.1
[58] Field of Search ................................ 435/69.1, 320.1, 435/419, 468; 536/24.1; 800/278, 283, 286, 287, 309, 317.4

[56] References Cited

U.S. PATENT DOCUMENTS

| | | | |
|---|---|---|---|
| 5,416,250 | 5/1995 | Ferro et al. | 800/205 |
| 5,512,466 | 4/1996 | Klee et al. | 435/172.3 |
| 5,723,746 | 3/1998 | Bestwick et al. | 800/205 |
| 5,750,864 | 5/1998 | Bestwick et al. | 800/205 |

OTHER PUBLICATIONS

Kay R, et al. "Duplication of CaMV 35S promoter sequences." Science 236: 1299–1302, Jun. 1987.

Benfey PN, et al. "The cauliflower mosaic virus 35S promoter: Combinatorial regulation of transcription in plants." Science 250: 959–966, Nov. 1990.

Kim Y, et al. "A 20 nucleotide upstream element is essential for the nopaline synthase (nos) promoter activity." Plant Mol. Biol. 24: 105–117 1994.

Cordes, S., et al., "Interaction of a Developmentally Regulated DNA–Binding Factor with Sites Flanking Two Different Fruit–Ripening Genes from Tomato," The Plant Cell 1:1025–1034 (1989).

Deikman, J., et al., "Control of Gene Transcription by Ethylene During Tomato Fruit Ripening," Biology and Biotechnology of the Plant Hormone Ethylene, A.K. Kanellis et al (eds.), Kluwer Acadmic Publishers, pp. 123–131, 1997.

Deikman, J., et al., "Interaction of a DNA binding factor with the 5'–flanking region of an ethylene–responsive fruit ripening gene from tomato," The EMBO Journal 7(11): 3315–3320 (1988).

Deikman, J., et al., "Organization of Ripening and Ethylene Regulatory Regions in a Fruit–Specific Promotor from Tomato (*Lycopersicon esculentum*)," Plant Physiol. 100:2013–2017 (1992).

Genbank Accession No. S44898 E4=fruit ripening gene, 1992.

Genbank Accession No. X13437 Tomato ethylene–responsive fruit ripening gene E8, 1995.

Montgomery, Julie, et al., "Identification of an ethylene–responsive region in the promoter of a fruit ripening gene," Proc. Natl. Acad. Sci USA 90:5939–5943 (1993).

Valles, M.P., et al, "Agrobacterium–mediated transformation of commercial melon (*Cucumis melo* L., cv. Amarillo Oro," Plant Cell Reports 13:145–148 (1994).

Xu, R., et al., "Ethylene control of E4 transcription during tomato fruit ripening involves two cooperative cis elements," Plant Molecular Biology 31: 1117–1127 (1996).

*Primary Examiner*—Amy J. Nelson
*Attorney, Agent, or Firm*—Linda R. Judge

[57] ABSTRACT

The present invention is directed to a synthetic hybrid promoter composed of polynucleotide segments derived from the E8 and E4 gene promoters. The hybrid promoter is capable of providing high-level expression of heterologous genes, particularly in transformed fruit. DNA constructs containing the E8-E4 hybrid promoter operably linked to an exemplary heterologous SAMase gene are effective in conferring a delayed ripening phenotype to transformed fruit.

14 Claims, 13 Drawing Sheets

```
AAGCTTTAAT TGGTTGAGAT TGAACGTAAT TCAAATTATT CTGAGCCCAA ACCCTTAAAA TTCTAGGCGG
TTATCTTTGT TTGAATTCAT TTTTGACATC CCTAATGATA TTGTTCACGT AATTAAGTTT TGTGGAAGTG
AGAGAGTCCA ATTTTGATAA GAAAAGAGTC AGAAAACGTA ATATTTTAAA AGTCTAAATC TTTCTACAAA
TAAGAGCAAA TTTATTTATT TTTTAATCCA ATAAATATTA ATGGAGGACA AATTCAATTC ACTTGGTTGT
AAAATAAACT TAAACCAATA ACCAAAGAVC TAATAAATCT GAAGTGGAAT TATTAAGGAT AATGTACATA
GACAATGAAG AAATAATAGG TTCGATGAAT TAATAATAAT TAAGGATGTT ACAATCATCA TGTGCCAAGT
ATATACACAA TATTCTATGG GATTTATAAT TTCGTTACTT CACTTAACTT TTGCGTAAAT AAAACGAATT
ATCTGATATT TTATAATAAA ACAGTTAATT AAGAACCATC ATTTTTAACA ACATAGATAT ATTATTTCTA
ATAGTTTAAT GATACTTTTA AATCTTTTAA ATTTTATGTT TCTTTTAGAA AATAAAAATT CAAAAAAATT
AAATATATTT ACAAAAACTA CAATCAAACA CAACTTCATA TATTAAAAGC AAAATATATT TTGAAAATTT
CAAGTGTCCT AACAAATAAG ACAAGAGGAA AATGTACGAT GAGAGACATA AAGAGAACTA ATAATTGAGG
AGTCCTATAA TATATAATAA AGTTTATTAG TAAACTTAAT TATTAAGGAC TCCTAAAATA TATGATAGGA
GAAAATGAAT GGTGAGAGAT ATTGGAAAAC TTAATAATTA AGGATNTTAA AATATATGGT AAAAGATAGG
CAAAGTATCC ATTATCCCCT TTTAACTTGA AGTCTACCTA GGCGCATGTG AAAGGTTGAT TTTTTGTCAC
GTCATATAGC TATAACGTAA AAAAAGAAAG TAAAATTTTT AATTTTTTTT AATATATGAC ATATTTTAAA
CGAAATATAG GACAAAATGT AAATGAATAG TAAAGGAAAC AAAGATTAAT ACTTACTTTG TAAGAATTTA
AGATAAATTT AAAATTTAAT AGATCAACTT TACGTTAAAG TAAACTTGGG TGGGTCAAGA CCCAACTCGA
TTTCTGTTCA ACCCATTTTA ATATTTCTAT TTTCAACCTA ACCCGCTCAT TTGATACCCC TACAAATATC
ATATTTGTGT GTGAAATATT TTTTGGGCTG GAGAGAGAGG CCCCGAGGGG AGTGGAGGGG TGGGGTGGGG
AGAGAGAGCG AGAAAGAGTG GAGAGAGAAA TTTGATATGA AATCCTACAT ATATTACAGA TTGTAATGTT
```

Fig. 2A

```
CTAAACTATA ACGATTTGTC ATAAACACAT ATCATGGATT TGTCTTTTTG TGTAATTTTC CCAATTGTAA

ATAGGACTTC GTTATTTGAA ACTTGAAAGT GAAGTCACAT AGATTAAGTA CAAACATTAA TTAAAGACCG

TGGTGGAATG ATAAATATTT ATTTATCTTT AATTAGTTAT TTTTTTGGGA GCTCTTTATT CCAATGTGAG

ACTTTTGCGA CATATATTCA AATTTAATCG AATCACAATA TGTATTAGAT TGATAAAAAA ATAATTTTTT

TACAATGTTA GTTGAGACTC ATAACTTACT GCCTATTGGT AATCTATGAC TCCTAATTCC TTAATTATTT

AAATATATCA TCTTGATCGT TAACAAAGTA ATTTCGAAAG ACCACGAGTA AGAAGACAAA CGAGAATACC

AAAAAATTCA AAAATTTAAT GTGATTTGGT CAATCGATCT ACGTCCATAA AGGAGATGAG TAATCTACTA

TAAATATGAG AGTACAAAAT ACAGAGAGAA ACAACCTCAA CTAATTCACT CGGAATACAT GAGAAGTTCA

CACAAGTGAT AACGTATCAA ACTTGTGACC CACACTTTTC CCTCTAACCA AGCTCTTAA AACTATATTG

TGAATGCTGA TTAAGTTAAA CGAAACAGTC CTAAATCTTT TCCGTCCTAT GAGAAACAAG ATTAATCAAT

TCACAATTTT TTTAAAAAGA AAAACCTGTA AGAAATTTAG GCAAACAAAA CCTAACACAA GTTTGTTTTT

GTTTTTACTA CCAACAAGAA ATTCAAATGG CAAATGTATA ACGCATCTTA GCTAATTATA TGACCAGATT

CAGATTAATA TACATCTTCA CCCATGCAAT CCATTTCTAT ATAAAGAAAC ATACACGAAC TTGATATTAT

TAGAGATTGA GCCATGG
```

Fig. 2B

```
CTTAAAATGTACGATGAGAGACATAAAGAGAACTAATAATTGAGGAGTCCTATAATATATAAT
AAAGTTTATTAGTAAACTTAATTATTAAGGACTCCTAAAATATATGATAGGAGAAAATGAATG
GTGAGAGATATTGGAAAACTTAATAATTAAGGATNTTAAAATATATGGTAAAAGATAGGCAAA
GTATCCATTATCCCCTTTTAACTTGAAGTCTACCTAGGCGCATGTGAAAGGTTGATTTTTTGT
CACGTCATATAGCTATAACGTAAAAAAAGAAAGTAAAATTTTAATTTTTTTAATATATGAC
ATATTTTAAACGAAATATAGGACAAAATGTAAATGAATAGTAAAGGAAACAAAGATTAATACT
TACTTTGTAAGAATTTAAGATAAATTTAAAATTTAATAGATCAACTTTACGTCTAGAAAGACC
CATATCTAGAAGGAATTTCACGAAATCGGCCCTTATTCAAAAATAACTTTTAAATAATGAATT
TTAAATTTTAAGAAATAATATCCAATGAATAAATGACATGTAGCATTTTACCTAAATATTTCA
ACTATTTTAATCCAATATTAATTTGTTTTATTCCCAACAATAGAAAGTCTTGTGCAGACATTT
AATCTGACTTTTCCAGTACTAAATATTAATTTTCTGAAGATTTTCGGGTTTAGTCCTCTTCGA
CACTTTTTTCACAATTTTTTTAAAAAGAAAAACCTGTAAGAAATTTAGGCAAACAAAACCTAA
CACAAGTTTGTTTTGTTTTACTACCAACAAGAAATTCAAATGGCAAATGTATAACGCATCT
TAGCTAATTATATGACCAGATTCAGATTAATATACATCTTCACCCATGCAATCCATTTCTATA
TAAAGAAACATACACGAACTTGATATTATTAGAGATTGAGCCATGG
```

Fig. 10

SYNTHETIC HYBRID TOMATO E4/E8 PLANT PROMOTER

This application claims priority to U.S. Provisional application Ser. No. 60/059,234, filed Sep. 18, 1997 expressly incorporated by reference herein.

FIELD OF THE INVENTION

The present invention relates to a synthetic E8-E4 hybrid promoter composed of polynucleotide segments derived from the tomato E8 and tomato E4 genes, and to DNA constructs, chimeric genes, vectors, kits, and transformation methods employing the promoter.

References

Adams, D. O., and Yang, S. F., *Plant Physiology* 70:117–123 (1977).

Ausubel, F. M., et al., in *CURRENT PROTOCOLS IN MOLECULAR BIOLOGY*, John Wiley and Sons, Inc., Media, Pa. (1992).

Ayub, R., et al., *Nature Biotechnology* 14:862–866 (1996).

Balague, C., et al., *Eur. J. Biochem.* 212:27–34 (1993).

Balazs, E., et al., *Gene* 19(3):239–249 (1982).

Becker, D., et al., *Plant Mol. Biol.* 20:1195–1197 (1992).

Bellini, C., et al., *Bio/Technology* 7(5):503–508 (1989).

Brunke, K. J. and Wilson, S. L., European Patent Publication No. 0 559 603 A2, published Sep. 08, 1993.

Comai, L., and Coning, A. J., U.S. Pat. No. 5,187,267, issued Feb. 16, 1993.

Cordes, S., et al., *The Plant Cell* 1:1025–1034 (1989).

Coupe, S. A. and Deikman, J., *The Plant Journal* 11(6):1207–1218 (1997).

Dayhoff, M. O., in *ATLAS OF PROTEIN SEQUENCE AND STRUCTURE* Vol. 5, National Biomedical Research Foundation, pp. 101–110, and Supp. 2, Vol. 5, pp. 1–10 (1972).

Deikman, J., et al., *Plant Physiol.* 100(4):2013–2017 (1992).

Deikman, J. and Fischer, R. L., *EMBO J.* 7:3315–3320 (1988).

Dong, J. Z., et al., *Bio/Technology* 9:858–863 (1991).

Fang, G., and Grumet, R., *Plant Cell Rep.* 9:160–164 (1990).

Fraley, R., et al., U.S. Pat. No. 5,352,605, issued on Oct. 4, 1994.

Gonsalves, C., et al., *J. Amer. Soc. Hort. Sci.* 119:345–355 (1994).

Good, X., et al., *Plant Mol. Biol.* 26:781–790 (1994).

Guilley, H., et al., *Cell* 30(3):763–773 (1982).

Hamilton, A. J., et al., *Nature* 346:284–287 (1990).

Hood, E., et al., *Transgenic Research* 2:208–218 (1993).

Hooykaas, P. J. J., and Schilperoot, R. A., in *TRENDS IN BIOCHEMICAL SCIENCES*, International Union of Biochemistry and Elsevier Science Publishers, v. 10(8):307–309 (1985).

Houck, C. M. and Pear, J. R., U.S. Pat. No. 4,943,674, issued Jul. 24, 1990.

Jefferson, R. A., *Plant Mol. Biol. Rep.* 5:387 (1987b).

Jefferson, R. A., et al., *EMBO J.* 6:3901 (1987a).

Jefferson, R. A., et al., *EMBO J.* 6:3901 (1987a).

Jefferson, R. A., *Plant Mol. Biol. Rep.* 5:387 (1987b).

Klee, H. J., et al., *Plant Cell* 3:1187–1193 (1991).

Klein, T. M., et al., *PNAS USA* 85(22):8502–8505 (1988).

Knessl, M. L. and Deikman, J., *Plant Physiology* 112:537–547 (1996).

Kramer, M. G., et al., in *BIOLOGY & BIOTECHNOLOGY OF THE PLANT HORMONE ETHYLENE* Kluwer Academic Publishers, The Netherlands (1996).

Laemmli, E. K., *Nature* 227:680–685 (1970).

Leisner, S. M., and Gelvin, S. B., *Proc. Natl. Acad. Sci. USA* 85(8):2553–2557 (1988).

Lin, E., et al., *Plant Mol. Biol.* 23:489–499 (1993).

Lincoln, J. E., et al. *Proc. Natl. Acad. Sci. U.S.A.*, 84:2793–2797 (1987).

Lincoln, J. E. and Fischer, R. L., *Mol. Gen. Genet.* 212:71–75 (1988).

Maniatis, T., et al., in *MOLECULAR CLONING: A LABORATORY MANUAL*, Cold Spring Harbor Laboratory, Cold Spring Harbor, N.Y. (1982).

Mariani, C., et al., *Nature* 357:384–387 (1992).

Mathews, H. V., et al., *In Vitro Cell Dev. Biol.* 28P:172–178 (1992).

Melchers, L. S., et al., *Plant J.* 5:469–480 (1994).

Miki, B. L. A., et al., *PLANT DNA INFECTIOUS AGENTS* (Hohn, T., et al., Eds.) Springer-Verlag, Vienna, Austria, pp. 249–265 (1987).

Montgomery, J., et al., *Plant Cell* 5:1049–1062 (1993).

Montgomery, J., et al., *Proc. Natl. Acad. Sci. U.S.A.* 90:5939–5943 (1993).

Mullis, K. B., et al., U.S. Pat. No. 4,683,195, issued Jul. 28, 1987.

Mullis, K. B., U.S. Pat. No. 4,683,202, issued Jul. 28, 1987.

Ni, M., et al., *Plant J.* 7:661–676 (1995).

Odell, J. T., et al., *Plant Mol Biol* 10(3):263–272 (1988).

Odell, J. T., et al., *Nature* 313:810–812 (1985).

Odell, J. T., et al., *J. Cell Biochem.* (Suppl. 11B):60 (1987).

Pearson, W. R., *Methods in Enzymol.* 183:63–98 (1990).

Pearson, W. R., and Lipman, D. J., *PNAS* 85:2444–2448 (1988).

Penarrubia, L., et al., *Plant Cell* 4:681–687 (1992).

Picton, S., et al., *Plant Physiology* 103(4):1471–1472 (1993).

Ponstein, A. S., et al., *Plant Physiol.* 104:109–118 (1994).

Rogers, S., U.S. Pat. No. 5,378,619, issued on Jan. 3, 1995.

Rogers, S., U.S. Pat. No. 5,034,322, issued on Jul. 23, 1991.

Saiki, R. K., et al., *Science* 239:487–491 (1988).

Sambrook, J., et al., in *MOLECULAR CLONING: A LABORATORY MANUAL*, Cold Spring Harbor Laboratory Press, Cold Spring Harbor, N.Y., Vol. 2 (1989).

Sato, T., and Theologis, A., *Proc. Natl. Acad. Sci. USA* 86:6621–6625 (1989).

Schuch, W., *Euphytica.* 79(3):287–291 (1994).

Sheehy, R. E., et al., *J. Bact.* 173:5260–5265 (1991).

Studier, F. W., et al., *J. Virol* 19:136 (1976).

Tommerup, H., et al., *Eur. Congr. Biotechnol.* 5:916–918 (1990).

Toubart, P., et al., *Plant J.* 3:367–373 (1992).

Valles, M. P. and Lasa, J. M., *Plant Cell Rep.* 13:145–148 (1994).

Van Haaren, M. J. J., et al., *Plant Mol. Bio.* 21:625–640 (1993).

Woloshuk, C. P., et al., *J. Plant Cell* 3:619–628 (1991).

Xu, R., et al., *Plant Mol. Biol.* 31:1117–1127 (1996).

Yoshioka, K., et al., *Jpn. J. Breeding* 42(2):278–285 (1992).

Zhu, Q., et al., *Plant Cell* 7:1681–1689 (1995).

BACKGROUND OF THE INVENTION

Promoters that regulate gene expression in plants are essential elements of plant genetic engineering. Several examples of promoters useful for the expression of selected genes in plants are now available (Zhu, et al., 1995; Ni, et al., 1995).

To be expressed in a cell, a gene must be operably linked to a promoter which is recognized by certain enzymes in the cell. The 5' non-coding regions of a gene (i.e., regions immediately 5' to the coding region), referred to as promoters or transcriptional regulatory regions, initiate transcription of the gene to produce a mRNA transcript. The mRNA is then translated at the ribosomes of the cell to yield an encoded polypeptide.

Promoters typically contain from about 500–1500 bases, and can provide regulated expression of genes under their control. Expression of heterologous genes or selected sequences of genes in transgenic plants has typically involved the use of constitutive promoters, i.e., promoters which drive the expression of a product throughout the plant at all times and in most tissues.

Promoters derived from viral genes are useful for expressing selected genes in plants. Examples of such viral genes which have been identified include those found in the caulimovirus family of viruses (a group of double-stranded DNA viruses), and include the Cauliflower Mosaic Virus (CaMV) 35S (Balazs, et al, 1982; Guilley, et al., 1982; Odell, et al., 1985; Odell, et al., 1987; Odell, et al., 1988; Tommerup, et al., 1990; Jefferson, et al., 1987a; Jefferson, 1987b) and CAMV 19S promoters (Fraley, et al., 1994), and the Figwort Mosaic Virus (FMV) (Rogers, 1995) promoter.

Promoters useful for regulating gene expression in plants and obtained from bacterial sources, e.g., Agrobacterium-derived promoters, have been identified and isolated. Such promoters include those derived from Agrobacterium T-DNA opine synthase genes, and include the nopaline synthase (nos) promoter (Rogers, 1991), the octopine synthase (ocs) promoter (Leisner and Gelvin, 1988) and mannopine synthase (mas) promoter.

Plant promoters (promoters derived from plant sources) effective to provide constitutive expression, are less well known, and include hsp80, Heat Shock Protein 80 from cauliflower, (Brunke and Wilson, 1993), and the tomato ubiquitin promoter (Picton, et al., 1993). These promoters can be used to direct the constitutive expression of heterologous nucleic acid sequences in transformed plant tissues.

The methods and results described herein demonstrate the ability to provide tissue and/or stage specific regulation of gene expression in transgenic plants. The tissue and/or stage-specific promoters of the present invention include a region of DNA that regulates transcription of the immediately adjacent (downstream) gene to a specific plant tissue. According to methods of the present invention, heterologous genes are linked to the promoters of the present invention.

Exemplary heterologous gene for the transformation of plants include genes whose products are effective to reduce ethylene biosynthesis in specific tissues of those plants, e.g. the fruits. An exemplary gene which impacts fruit ripening is the bacteriophage T3 gene encoding S-adenosylmethionine hydrolase (SAMase), Kramer, et al., (1996); Good, et al., (1994).

A limited number of inducible and/or tissue specific promoters are known. Promoters that provide fruit-specific expression include the E4 and E8 promoter from tomato (Cordes, et al., 1989; Bestwick, et al., 1995), and corresponding promoters from other plants which have substantially the same biological activity. The tomato E4 promoter is both stage and tissue specific (Cordes, et al., 1989), and typically, E4 mRNA is abundant in ripening tomato fruit and is not detected in leaf, root, stem, or unripe fruit. The E4 and E8 promoters are also ethylene responsive promoters, i.e., transcription of genes placed under their control is activated by ethylene. The E4 promoter requires ethylene for activation, while the E8 promoter is controlled by ethylene as well as by separate developmental signals (Deikman et al., 1997). Another fruit-specific promoter is the tomato 2AII gene promoter. It has been demonstrated that nucleic acid sequences placed under the regulatory control of the 5' non-coding region of the tomato 2AII gene (Van Haaren) are preferentially transcribed in developing fruit tissue. Fruit specific regulation of the kiwifruit actinidin promoter has been reported to be conserved in transgenic petunia plants (Lin, et al., 1993).

At present, a relatively small number of plant promoters, particularly constitutive plant promoters, have been identified. The use of such promoters in plant genetic engineering has been rather limited to date, since gene expression in plants is, for the most part, typically tissue, developmentally, or environmentally-regulated.

A need exists for tissue and developmental stage specific promoters that are functional in plant cells, and which are capable of providing high level expression of heterologous genes.

SUMMARY OF THE INVENTION

The present invention is directed to a synthetic promoter composed of a combination of cis-acting elements derived from the transcriptional regulatory sequences of the E8 and E4 genes, as exemplified by tomato. The synthetic hybrid promoter allows high-level, fruit specific expression of nucleic acid sequences placed under its control.

In one aspect, the invention provides a DNA construct which contains a DNA coding sequence under the transcriptional control of a hybrid E8-E4 promoter. The DNA coding sequence is typically heterologous to the hybrid promoter and is operably linked to the promoter to enable expression of the product. Exemplary products include, but are not limited to S-adenosylmethionine hydrolase (SAMase), amino-cyclopropane-1-carboxylic acid (ACC) deaminase, ACC oxidase antisense molecule, ACC synthase antisense molecule, ACC oxidase cosuppression molecule, ACC synthase cosuppression molecule, thaumatin, sucrose phosphate synthase and lycopene cyclase.

The E8-E4 hybrid promoter of the invention is composed of a polynucleotide segment derived from an E8 gene promoter which is fused to a polynucleotide segment derived from an E4 gene promoter positioned downstream of the E8 promoter segment. The E8 promoter-derived polynucleotide segment includes at least 30 contiguous nucleotides selected from the region extending from nucleotide positions −2257 to −847 of the tomato E8 promoter which corresponds to approximately nucleotides 1 to 1411 of SEQ ID NO:7, or the functional equivalent thereof. The polynucleotide segment derived from an E4 gene promoter includes at least 200 contiguous nucleotides selected from the region extending from nucleotide positions −1150 to +16 of the tomato E4 promoter which corresponds to approximately nucleotides 271 to 1437 of SEQ ID NO:8, or the functional equivalent thereof. The particular combination of E8 and E4 polynucleotide segments produces a hybrid promoter which is effective to drive expression of a heterologous gene (e.g., a reporter gene) at a level of at least about 75–300% of the expression level obtained using either an unmodified E4 or E8 gene promoter.

In one embodiment of the hybrid promoter, the nucleotide sequence of the E8 promoter segment corresponds to nucleotides −1529 to −847 of the tomato E8 promoter, or the functional equivalent thereof, which corresponds to approximately nucleotides 3 to 686 of SEQ ID NO:6 and nucleotides 729 to 1411 of SEQ ID NO:7. The hybrid promoter also contains an E4 promoter segment corresponding to nucleotides −315 to +16 of the tomato E4 promoter, or the functional equivalent thereof, which corresponds to approximately nucleotides 693 to 1023 of SEQ ID 6 or nucleotides 1107 to 1437 of SEQ ID NO:8, referred to herein as the "short E8-E4 hybrid promoter".

In another embodiment of the hybrid promoter, the nucleotide sequence of the E8 promoter segment corresponds to nucleotides −2257 to −1103 of the tomato E8 promoter, or the functional equivalent thereof, which corresponds to approximately nucleotides 1 to 1160 of SEQ ID NO:1 and nucleotides 1 to 1156 of SEQ ID NO:7. The hybrid promoter also contains an E4 promoter segment corresponding to nucleotides −1150 to +16 of the tomato E4 promoter, or the functional equivalent thereof, which corresponds to approximately nucleotides 1157 to 2323 of SEQ ID 1 or nucleotides 271 to 1437 of SEQ ID NO:8, designated herein as the "long E8-E4 promoter".

In one respect, the E8-E4 hybrid promoter of the present invention can be used to reduce ethylene production in transformed fruit cells, to thereby alter the ripening phenotype of transgenic fruit composed of such fruit cells.

In another embodiment, the DNA sequence can correspond to a pathogenesis related gene, such as polygalacturonase inhibiting protein (PGIP), glucanase and chitinase.

The present invention also includes the use of any of the above chimeric gene constructs to generate a plant transformation vector. Such vectors can be used in any plant cell transformation method, including Agrobacterium-based methods, electroporation, microinjection, and microprojectile bombardment. These vectors may form part of a plant transformation kit. Other components of the kit may include, but are not limited to, reagents useful for plant cell transformation.

In another embodiment, the invention includes a plant cell, plant tissue, transgenic plant, fruit cell, whole fruit, seeds or calli containing any of the above-described chimeric genes and the corresponding expressed gene products. Preferred plants are dicots such as melon, strawberry, raspberry, and tomato, and particularly Cucumis sp (e.g., *Cucumis melo*).

In another aspect of the present invention, the hybrid promoters described herein are employed in a method for delaying ripening of fruit from a fruit-bearing plant. In this method, a transgenic plant containing the chimeric gene of the present invention is grown to produce a transgenic plant bearing fruit. In one particular embodiment, the chimeric gene encodes a product capable of reducing ethylene biosynthesis when expressed in plant cells (e.g., S-adenosylmethionine hydrolase, amino-cyclopropane-1-carboxylic acid (ACC) deaminase, ACC oxidase antisense molecule, ACC synthase antisense molecule, ACC oxidase cosuppression molecule, ACC synthase cosuppression molecule). Fruit produced by these transgenic plants have a modified ripening phenotype. A modified ripening phenotype refers to an alteration of the rate of ripening (e.g., an increased time course, or delay of ripening) of a transgenic fruit relative to corresponding (i.e., non-transgenic) wild-type fruit.

Further, the invention includes a method for producing a transgenic plant such as a fruit-bearing plant. In this method, the chimeric gene of the present invention, typically carried in an expression vector allowing selection in plant cells, is introduced into progenitor cells of selected plant. These progenitor cells are then grown to produce a transgenic plant bearing fruit.

Yet another aspect of the invention is directed to a method for conferring enhanced expression activity to an E4 promoter. In the method, a polynucleotide segment of at least 30 contiguous nucleotides selected from the region extending from nucleotide positions −2257 to −847 of the tomato E8 promter which corresponds to approximately nucleotides 1 to 1411 of SEQ ID NO:7, or the functional equivalent thereof, is fused in an upstream orientation to an E4 promoter polynucleotide segment of at least 200 contiguous nucleotides selected from the region extending from nucleotide positions −1150 to +16 of the tomato E4 promter which corresponds to approximately nucleotides 271 to 1437 of SEQ ID NO:8, or a functional equivalent thereof, to form a hybrid E8-E4 promoter capable of regulating expression of a heterologous gene operably linked thereto. The hybrid promoter is effective to drive expression of the heterologous gene to a greater degree than the unmodified E4 promoter, and preferably at a level of at least about 75–300% of the expression level obtained by using an unmodified E4 gene promoter. The hybrid promoter is also ethylene inducible and is capable of directing fruit-specific expression.

These and other objects and features of the invention will become more fully apparent when the following detailed description is read in conjunction with the accompanying figures and examples.

BRIEF DESCRIPTION OF THE FIGURES

FIGS. 2A–2B correspond to the nucleotide sequence of the long (large) E8-E4 promoter of the present invention (SEQ ID NO:1);

FIG. 10 presents the nucleotide sequence of the short (small) E8-E4 promoter of the present invention (SEQ ID NO:6);

DETAILED DESCRIPTION OF THE INVENTION

I. Definitions

Figure 1:
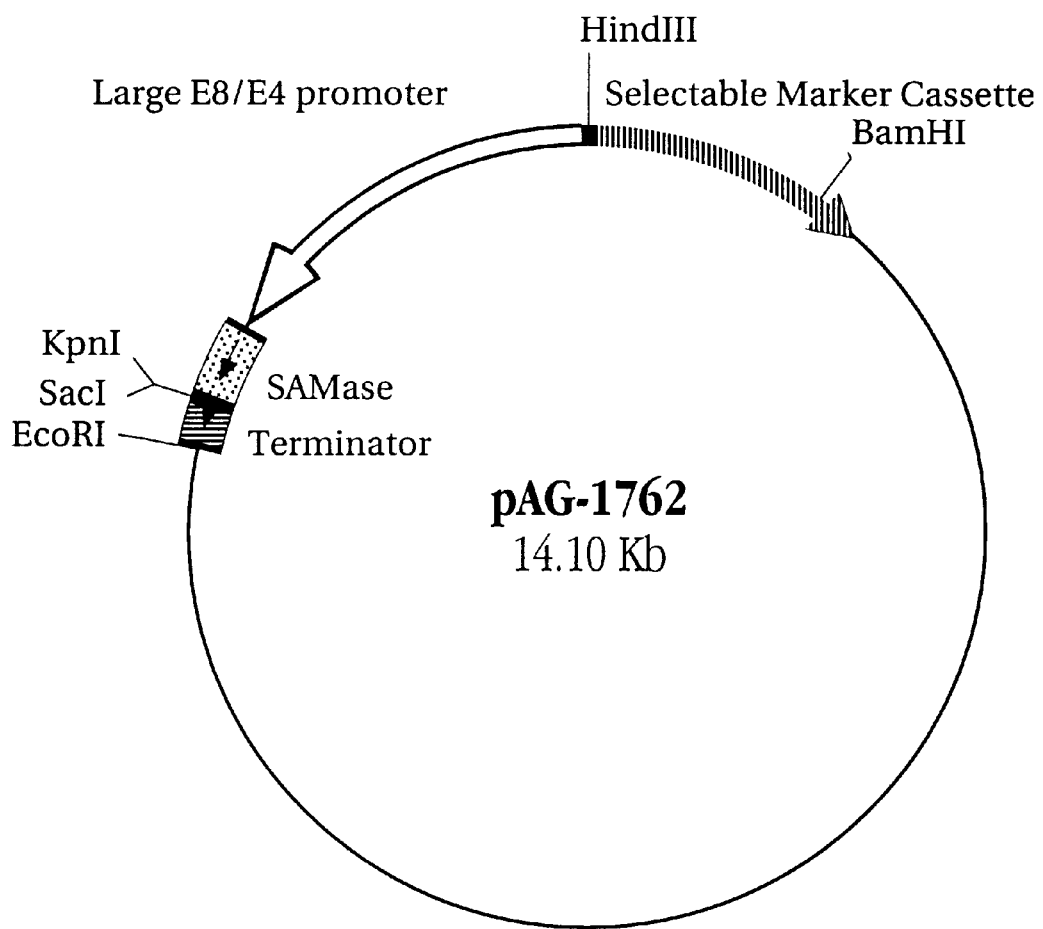
FIG. 1 presents a schematic description of the details of the construction of vector pAG-1762 (14.10 kb)

The term "polynucleotide" as used herein refers to a polymeric molecule having a backbone that supports bases capable of hydrogen bonding to typical polynucleotides, where the polymer backbone presents the bases in a manner to permit such hydrogen bonding in a sequence specific fashion between the polymeric molecule and a typical polynucleotide (e.g., single-stranded DNA). Such bases are typically inosine, adenosine, guanosine, cytosine, uracil and thymidine. Polymeric molecules include double and single stranded ribonucleic acids (RNA) and deoxyribonucleic acids (DNA), and may include polymers having backbone modifications such methylphosphonate linkages.

The term, "recombinant nucleic acid" as used herein refers to nucleic acid, originally formed in vitro, in general, by the manipulation of nucleic acid by endonucleases, in a form not normally found in nature.

A "heterologous" DNA coding sequence is a structural coding sequence that is not native to the plant being transformed, or a coding sequence that has been engineered for improved characteristics of its protein product. Heterologous, with respect to the promoter, refers to a coding sequence that does not exist in nature in the same gene with the promoter to which it is currently attached.

Nucleic acid subunits are referred to herein by their standard base designations; T, thymine; A, adenosine; C, cytosine; G, guanine, U, uracil; variable positions are referred to by standard IUPAC abbreviations: W, A or T/U; R, A or G; S, C or G; K: G or T/U (37 CFR. §1.822).

The nucleic acid may be double stranded, single stranded, or contain portions of both double stranded or single stranded sequence. The depiction of a single strand also defines the sequence of the other strand and thus also includes the complement of the sequence.

A "heterologous" DNA or gene sequence encodes a gene product not normally contiguous or associated with the promoter (e.g., an E8-E4 hybrid promoter adjacent DNA sequences encoding S-adenosylmethionine cleaving enzyme). In the context of the present invention, a heterologous gene is any DNA sequence other than the E8 or E4 gene sequence.

"Regulatable promoter" is any promoter whose activity is affected by a cis or trans acting factor (e.g., an ethylene-inducible promoter such as the tomato E8 promoter).

"Constitutive promoter" is any promoter that directs RNA production in many or all tissues of a plant transformant at most times.

A "tissue-specific promoter" is any promoter which directs RNA synthesis at higher levels in particular types of cells and tissues (e.g., a fruit specific promoter);

By "promoter" or "promoter segment" (e.g., a tomato E8 or E4 promoter segment) is meant a sequence of DNA that functions in a hybrid promoter disclosed herein to direct transcription of a downstream heterologous gene, and includes promoter or promoter segments derived by means of ligation with operator regions, random or controlled mutagenesis, addition or duplication of enhancer sequences, addition or modification with synthetic linkers, and the like, having promoter activity the functional equivalent of, the E8-E4 hybrid promoter described herein or pertinent regions thereof.

By "plant promoter" is meant a promoter or promoter region (as defined above), which in its native form, is derived from plant genomic DNA. The hybrid promoter of the present invention is a plant promoter.

By an E8 or an E4 gene promoter is meant a promoter obtained from an E8 or E4 gene considered to share sequence identity with the tomato E8 or E4 gene sequences described herein, or a particular region or regions thereof, or from a gene having at least about 70%, preferably about 80%, more preferably about 85%, even more preferably about 90% sequence identity over a length of polynucleotide sequence corresponding to the tomato E8 or tomato E4 gene sequences described herein.

Alternatively, an E4 or E8 gene promoter is obtained from the gene encoding an E8 or E4 protein wherein the amino acid sequence of the E4 or E8 protein has at least about 70%, preferably about 80%, more preferably about 85%, even more preferably about 90% sequence identity over a length of polypeptide sequence corresponding to the tomato E8 or tomato E4 polypeptide sequences of SEQ ID NO:10 and SEQ ID NO:9, respectively.

The term "homology" or "homologue" as used herein refers to the level of identity between two sequences, i.e. 70% homology means the same thing as 70% sequence identity as determined by the algorothims described below, and accordingly a homologue of a given sequence has at least about 70%, preferably about 80%, more preferably about 85%, even more preferably about 90% sequence identity over a length of the given sequence.

"Promoter strength" refers to the level of promoter-regulated expression of a heterologous gene in a plant tissue or tissues, relative to a suitable standard (e.g., a hybrid E8-E4 promoter from a particular plant, e.g., tomato, versus either the tomato E8 gene or tomato E4 gene promoter alone). Expression levels can be measured by linking the promoter to a suitable reporter gene such as GUS (β-glucuronidase), dihydrofolate reductase, or nptII (neomycin phosphotransferase II). Expression of the reporter gene can be easily measured by fluorometric, spectrophotometric or histochemical assays (Jefferson, et al., 1987a; Jefferson, 1987b).

For the purposes of the present invention, a high level E4/E8 hybrid promoter is one that drives expression of a particular gene, such as a reporter gene, at about 75–300% of the levels obtained with either the non-hybrid E4 or E8 gene promoter derived form the same source.

"Nucleic acid sequence identity" is determined essentially as follows. Two polynucleotide sequences of the same length are considered to be identical to one another, if, when they are aligned using the ALIGN program, over 60%, preferably about 70%, preferably about 80%, more preferably about 85%, even more preferably about 90% sequence are determined to be identical when aligned using the default parameters and the default PAM matrix (Dayhoff, 1972). The ALIGN program is found in the FASTA version 1.7 suite of sequence comparison programs (Pearson and Lipman, 1988; Pearson, 1990; program available from William R. Pearson, Department of Biological Chemistry, Box 440, Jordan Hall, Charlottesville, Va.).

"Amino acid sequence identity" with respect to the amino acid sequences identified herein is defined as the percentage of amino acid residues in a candidate sequence that are identical with the amino acid residues in the native sequence, after aligning the sequences and introducing gaps, if necessary, to achieve the maximum percent sequence identity, and not considering any conservative substitutions as part of the sequence identity. Such amino acid sequence identity may be determined using the ALIGN program, with default parameters as described above.

By "functional equivalent" is meant a nucleic acid sequence which corresponds to an active E4 or E8 promoter wherein the E4 or E8 gene product expressed by the active E4 or E8 promoter has at least about 80% amino acid sequence identity with the E4 or E8 gene product having the amino acid sequence shown in SEQ ID NOs:10 or 9, respectively. The functional equivalent of an E4 or E8 promoter includes, for instance, an E4 or E8 promoter which has a nucleic acid sequence that is the same as part of, but not all of, the nucleic acid sequence of the E4 or E8 promoter and which either retains essentially one or more of the same biological functions or activities as a full length E4 or E8 promoter, e.g., the tomato E4 or E8 promoter, as described herein.

Two nucleic acid fragments are considered to be "selectively hybridizable" to a reference polynucleotide if they are capable of specifically hybridizing to the polynucleotide or variants thereof or of specifically priming a polymerase chain amplification reaction: (i) under moderately stringent hybridization and wash conditions, as described, for example, in Maniatis, et al. (1982), pages 320–328, and 382–389; (ii) using reduced stringency wash conditions that allow at most about 25–30% base pair mismatches, for example: 2×SSC (contains sodium 3.0 M NaCI and 0.3 M sodium citrate, at pH 7.0), 0.1% sodium dodecyl sulfate (SDS) solution, room temperature twice, 30 minutes each; then 2×SSC, 0.1% SDS, 37° C., once, for 30 minutes; then 2×SSC, at room temperature twice, for 10 minutes each, or (iii) selecting primers for use in typical polymerase chain reactions (PCR) under standard conditions (for example, in Saiki, et al., 1988), which result in specific amplification of sequences of the desired target sequence or its variants.

As used herein, a "plant cell" refers to any cell derived from a plant, including undifferentiated tissue (e.g., callus) as well as plant seeds, pollen, progagules and embryos.

II. Inducible Promoters for Expression of Genes in Plants and the Role of Ethylene The present invention is directed to the applicants' discovery of a hybrid promoter prepared by a combination of regions derived from an E8 and an E4 promoter that is capable of directing high level expression of heterologous genes.

In preparing transgenic plants, a desirable feature is the ability to express an introduced transgene in response to a particular stimulus, or to localize its expression to certain tissues. In an effort to develop new tissue-specific and/or developmentally activated promoters capable of directing high level expression of a heterologous gene in plants, it was discovered that a combination of regions derived from the tomato E8 and E4 promoters, when ligated in a 5' to 3' fashion, were capable of providing such a promoter.

To summarize, the present invention is based upon the surprising discovery of a high-level hybrid E8-E4 promoter which (i) is capable of driving expression of a heterologous gene at significantly greater levels than either the unmodified E8 or E4 promoters alone, (ii) retains the fruit and ripening-specific function of the parent regulatory regions and (iii) is effective in the plant from which the E4 and E8 promoter sequences were derived (e.g., tomato), as well as in other plants (e.g., muskmelon, apple and pear).

The parent promoters from which the hybrid promoter is derived were selected due to a number of features, and in particular, their ability to regulate expression of the SAMase gene in ripening tomato fruit (Lincoln and Fischer, 1988; Lincoln, et al., 1987).

The SAMase gene encodes the enzyme S-adenosylmethionine hydrolase. The isolation, cloning and sequence of the SAMase gene is described in U.S. Pat. No. 5,589,623, and in International PCT Publication No. WO 95/35387. This enzyme, encoded by the *E. coli* bacteriophage T3, hydrolyzes AdoMet to homoserine and MTA. The enzyme is referred to as AdoMet hydrolase (AdoMetase), or by its other name, S-adenosylmethionine cleaving enzyme (SAMase) (Studier, et al.). When expressed in plant cells, AdoMetase is effective to "short circuit" a branch of the biosynthetic pathway that produces ethylene, thereby reducing ethylene production in transgenic plants expressing the gene.

The effects of ethylene on plants, whether produced by the plant itself or applied exogenously, are numerous and of considerable commercial importance. Among the diverse physiological effects are leaf abscission, fading and wilting of flowers, leaf yellowing, leaf epinasty, and stimulation of ripening in fruits and vegetables. Of even greater significance is the fact that ethylene promotes senescence (a natural, genetically controlled degenerative process which typically leads to death) in plants, both in selected groups of cells and in whole organs, such as, fruits, leaves, or flowers.

Normally, ethylene production from plant tissue is low. Large quantities of ethylene, however, are produced during ripening and senescence processes, and are also produced following trauma. In fruits and vegetables, the stimulation of ethylene production by cuts or bruises can bear considerably on the effectiveness of storage. Ethylene-induced leaf browning is a common basis for loss in many plants, including lettuce and tobacco. In some tissues, exposure to only a small amount of ethylene may cause an avalanche of ethylene production in adjacent plants or plant tissues such as fresh produce. This autocatalytic effect can be very pronounced and lead to loss of fruit quality during transportation and storage.

Thus, in one aspect, the present invention provides a method to regulate plant cell expression of any gene in a tissue or development stage-specific manner, in particular, genes whose products reduce ethylene synthesis in plant cells, using a hybrid promoter of the type described herein.

Returning now to the tomato E8 and E4 genes from which segments of the exemplary hybrid promoter are derived, the intact parent promoters, the tomato E8 and the tomato E4 promoter, are ethylene inducible (Deikman, et al., 1992; Xu, et al., 1996).

The tomato E4 and E8 promoters may be used to isolate functionally equivalent promoters from other plants. For example, the raspberry E4 promoter may be obtained from a raspberry homologue of the tomato E4 gene. Accordingly, the tomato E4 and E8 promoters can be used to isolate functionally equivalent promoters or partial sequences thereof from additional other types of plants, and those promoter sequences used to make hybrid E4/E8 promoters.

III. Construction of a Hybrid E8-E4 Promoter

The E8-E4 hybrid promoter contains a combination of nucleotide segments as exemplified by those derived from the tomato E8 and E4 genes. These segments, when combined in a 5'-to-3' fashion, are capable of providing a promoter having certain features, as will be described below.

The component polynucleotide segments of the hybrid promoter were determined on the basis of experiments conducted in support of the invention, as described in Examples 1–7.

The E8-E4 hybrid promoter is composed of a polynucleotide segment derived from an E8 gene promoter which is fused to a polynucleotide segment derived from an E4 gene promoter positioned downstream of the E8 promoter segment. The E8 promoter-derived polynucleotide segment preferably includes at least 30 contiguous nucleotides selected from the region extending from nucleotide positions −2257 to −847 of the tomato E8 promoter which corresponds to approximately nucleotides 1 to 1411 of SEQ ID NO:7, or the functional equivalent thereof. The E8 promoter sequence of SEQ ID NO:7 consists of the E8 promoter described by Deikman and Fischer, 1988 and Deikman, et al., 1992, extended on the 5' end, as described in Example 1. The polynucleotide segment derived from a E4 gene promoter preferably includes at least 200 contiguous nucleotides selected from the region extending from nucleotide positions −1150 to +16 of the tomato E4 promter which corresponds to approximately nucleotides 271 to 1437 of SEQ ID NO:8, or the functional equivalent thereof.

The construction of exemplary vectors containing the hybrid promoter is typically carried out as described in Examples 1–6. The sequence of the tomato E8 promoter for use in the present invention is provided in SEQ ID NO:7, and the DNA sequence of regions relevant to the examples of the present invention are provided in FIGS. 2A and 2B (SEQ ID NO:1) and FIG. 10 (SEQ ID NO:6), respectively. The sequence of the tomato E4 promoter has also been published (Cordes, et al., 1989), and the DNA sequences corresponding to segments pertinent to the invention are similarly provided in FIGS. 2A and 2B (SEQ ID NO:1) and FIG. 10 (SEQ ID NO:6), respectively.

Polynucleotide segments used to construct the hybrid promoter can be obtained by PCR amplification of tomato genomic DNA, using primers designed on the basis of the information presented herein, coupled with a multifunctional sequence analysis program, e.g., OLIGO version 5.0 for MacIntosh from National Biosciences, Inc. (Plymouth, Minn.), as detailed in Example 3.

Representative methods for isolating and characterizing an E4 and/or E8 promoter which can be applied for the purpose of obtaining a promoter segment of the present invention are described in International PCT Publication WO 95/35387.

Figure 11:
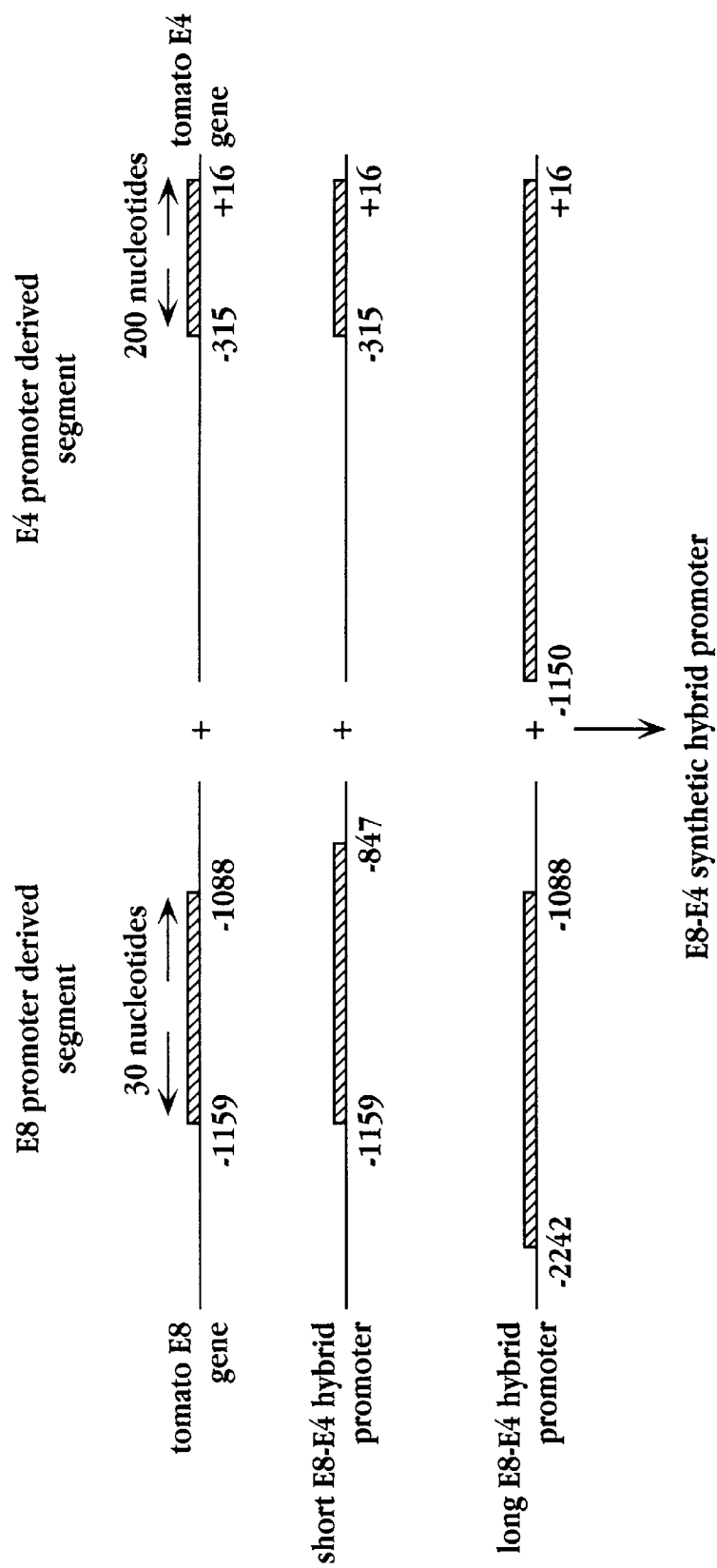
FIG. 11 is a schematic representation of active polynucleotide segments derived from the tomato E8 and E4 promoters which were utilized to prepare the hybrid promoters of the present invention.

The polynucleotide segments which make up the hybrid promoter were determined on the basis of expression results for transgenes driven by two representative hybrid promoters (FIG. 11), the long E8-E4 hybrid promoter (SEQ ID NO:1) and the short E8-E4 hybrid promoter (SEQ ID NO:6). Both versions of the hybrid promoter were highly effective in driving expression of an exemplary transgene coding for SAMase, as indicated by Western blot results shown in FIGS. 6 and 7, which depict the results of studies on expression of SAMase driven by hybrid E4/E8 promoters derived from tomato in musk melon. The hybrid promoters were significantly more active in driving expression than either the tomato E8 or tomato E4 promoter.

The exemplary long E8/E4 hybrid promoter contains an E8 polynucleotide segment corresponding to nucleotides from about −2257 to −1103 of a tomato E8 promoter, while the short E8/E4 hybrid promoter contains an E8 polynucleotide segment corresponding to nucleotides from about −1529 to −847 of the E8 promoter. In expression experiments carried out in support of the invention, the short E8 promoter segment was generally found to function as effectively as the long E8 promoter segment to enhance overall activity of the hybrid promoter. This was surprising in view of previous reports indicating that DNA sequences necessary for both ethylene responsiveness and overall mRNA levels reside in the E8 promoter region encompassed by the longer E8/E4 hybrid promoter and not the shorter version (Deikman, et al., 1992).

The E8 polynucleotide region encompassed by both versions of the hybrid promoter spans positions from about −2257 to −847 of the tomato E8 promter. On the basis of these results, hybrid promoters of the invention will contain an E8 promoter-derived polynucleotide segment which preferably includes at least 30 contiguous nucleotides selected from this region. In one particular embodiment of the invention, the segment will include at least about 40 nucleotides selected from this region. In yet another embodiment, that the segment will include at least about 50 contiguous nucleotides. It will of course be appreciated that the E8-derived polynucleotide may contain fewer than 30 contiguous nucleotides, and in some instances, may contain from about 15–25 contiguous nucleotides.

The suitability of a particular E8 segment for use in constructs employing the hybrid promoter can be evaluated in expression experiments employing a heterologous reporter gene. A particular E8 segment selected according to the above guidelines is ligated to a downstream E4 promoter segment using the methods described herein. Expression levels of a suitable reporter gene driven by the resulting hybrid E8/E4 promoter are then compared to expression levels for the same gene regulated by the corresponding E8 or E4 promoter alone.

An E8 polynucleotide segment suitable for forming a hybrid promoter is one which, when combined with an E4 promoter polynucleotide segment corresponding to those described herein and placed in a hybrid promoter, drives expression of a reporter gene at a level of at least about 75–300% of the expression level obtained using either an unmodified E4 or E8 gene promoter operably linked to said reporter.

A reporter gene, such as GUS ($\beta$-glucuronidase), can be used for this purpose. Expression of GUS protein can be easily measured by fluorometric, spectrophotometric or histochemical assays (Jefferson, 1987).

Turning now to the E4 polynucleotide segment of the hybrid promoter, an examination of the long E8/E4 hybrid promoter reveals an E4 polynucleotide segment corresponding essentially to the full-length E4 promoter, while the short E8/E4 hybrid promoter contains an E4 segment spanning from nucleotide positions −315 to +16 of the E4 promoter. As discussed above, both illustrative versions of the hybrid E8/E4 promoter were effective in directing expression of a heterologous gene (e.g., Examples 5 and 6). The high activity of the short E8/E4 hybrid was surprising, since studies on the E4 promoter alone indicate that both upstream and downstream elements are required for ethylene-responsive transcription (Xu, et al., 1996).

The E4 polynucleotide region encompassed by both versions of the hybrid promoter spans nucleotide positions from about −1150 to +16 of the tomato E4 promter. On the basis of these results, hybrid promoters of the invention will contain an E4 promoter-derived polynucleotide segment which preferably includes at least 200 contiguous nucleotides selected from this region. In one particular embodiment of the invention, the segment will include at least about 220 contiguous nucleotides selected from this region. In yet another embodiment, it is contemplated that the segment will include at least about 275 contiguous nucleotides. It will of course be appreciated that the E4-derived polynucleotide may contain fewer than 200 contiguous nucleotides, and may in some instances, contain from about 150–200 contiguous nucleotides.

Segments derived from the E4 gene will be selected and evaluated essentially as described above for the E8 component. Moreover, it will be appreciated that the above-described segments refer to functional equivalents thereof, and encompass promoters or promoter segments derived by means of ligation with operator regions, random or controlled mutagenesis, addition or duplication of enhancer sequences, addition or modification with synthetic linkers, and the like, having promoter activity similar to the E8-E4 hybrid promoter described herein or pertinent regions thereof.

IV. Chimeric Genes, Vector Construction and Plant Transformation

The E8/E4 hybrid promoter of the invention can be used to regulate expression of heterologous genes.

In support of the present invention, two exemplary chimeric genes containing an E8/E4 hybrid promoter sequence operably linked to a heterologous DNA sequence, were constructed, long E8/E4:SAMase (pAG-7162) and short E8/E4:SAMase (Examples 1 and 3). SAMase has been predicted to function more efficiently if expressed (i) in high levels and (ii) in a tissue specific manner. Accordingly, the hybrid promoter described herein represents an ideal promoter to satisfy this objective, and can be used to express any heterologous gene fitting the above-description.

A. Plant Transformation Vectors

Plant transformation vectors, containing an E8/E4 hybrid promoter/transcription-regulatory sequence, are constructed according to methods known in the art (see, for example, Houck and Pear, 1990, and Becker, et al., 1992).

The present invention provides vectors suitable for the transformation of plants. The vectors, chimeric genes and DNA constructs of the present invention are also useful for the expression of heterologous genes. Transgenic plants, and their fruit products, carrying the chimeric genes of the present invention, may be a useful source of recombinantly-expressed material.

In one embodiment, the chimeric genes of the present invention have two components: (i) a hybrid E8/E4 promoter and (ii) a heterologous DNA coding sequence.

The vectors of the present invention may be constructed to carry an expression cassette containing an insertion site for DNA coding sequences of interest. The transcription of such inserted DNA is then under the control of a suitable E8/E4 hybrid promoter (e.g., corresponding to SEQ ID NOs:1, 6).

Such expression cassettes may have single or multiple transcription termination signals at the coding-3'-end of the DNA sequence being expressed. The expression cassette may also include, for example, DNA sequences encoding (i) a leader sequence (e.g., to allow secretion or vacuolar targeting), and (ii) translation termination signals.

Further, the vectors of the present invention may include selectable markers for use in plant cells (such as the nptII kanamycin resistance gene). The vectors may also include sequences that allow their selection and propagation in a secondary host, such as, sequences containing an origin of replication and a selectable marker. Typical secondary hosts include bacteria and yeast. In one embodiment, the secondary host is *Escherichia coli*, the origin of replication is a colE1-type, and the selectable marker is a gene encoding ampicillin resistance. Such sequences are well known in the art and are commercially available (e.g., Clontech, Palo Alto, Calif.; Stratagene, La Jolla, Calif.).

The vectors of the present invention may also be modified to intermediate plant transformation plasmids that contain a region of homology to an *Agrobacterium tumefaciens* vector, a T-DNA border region from *Agrobacterium tumefaciens*, and chimeric genes or expression cassettes. Further, the vectors of the invention may comprise a disarmed plant tumor inducing plasmid of *Agrobacterium tumefaciens*. Other suitable vectors may be constructed using the promoters of the present invention and standard plant transformation vectors, which are available both commercially (Clontech, Palo Alto, Calif.) and from academic sources (Waksman Institute, Rutgers, The State University of New Jersey, Piscataway, N.J.).

The vectors of the present invention are useful for tissue and/or stage-specific expression of nucleic acid coding sequences in plant cells. For example, a selected peptide or polypeptide coding sequence can be inserted in an expression cassette of a vector of the present invention. The vector is then transformed into host cells, the host cells cultured under conditions to allow the expression of the protein coding sequences, and the expressed peptide or polypeptide isolated from the cells. Transformed progenitor cells can also be used to produce transgenic plants bearing fruit.

Further, the invention includes a method for producing a transgenic fruit-bearing plant, where fruit produced by the plant has a modified phenotype. In this method a chimeric gene is introduced (e.g., by transformation) into progenitor cells of the plant. An exemplary chimeric gene is composed of (i) a DNA sequence encoding a gene product effective to modify a phenotypic characteristic of the plant, e.g., to reduce ethylene biosynthesis in fruit produced by the plant, operably linked to (ii) a promoter whose expression is inducible, e.g., during fruit ripening, by a plant cytokine, or by ethylene synthesis by the fruit. As above, the DNA sequence is heterologous to the promoter and the chimeric gene contains the appropriate regulatory elements necessary for expression in a plant. Transformed progenitor are grown cells to produce a transgenic plant bearing fruit. The method further includes transforming progenitor cells of the plant with a selectable vector containing the chimeric gene. The DNA sequences and promoters may be as described above.

In one aspect of the invention, fruit produced by such transgenic plants has a reduced level of ethylene synthesis by the fruit. The fruit then demonstrates a modified ripening phenotype in which the time course of ripening is delayed.

The vectors, chimeric genes and DNA constructs of the present invention can be sold individually or in kits for use in plant cell transformation and the subsequent generation of transgenic plants.

B. Isolation of E4 and E8 Promoters

The E4 and/or E8 promoter may be obtained from a homologue of the tomato E4 or E8 gene. To detect the presence of an E4 or E8 gene in various plant species, e.g., strawberry, melon, carnation, cauliflower or raspberry, a southern blot experiment is carried out.

E4 or E8 homologues are identified in a Southern blot of the genomic DNA of a plant of interest, probed with a labeled DNA fragment containing the coding sequence of, e.g., the tomato E4 or E8 gene.

Preferably, the probe is selected to contain the coding sequence of the tomato E4 or E8 gene rather than the promoter sequence, since coding sequences are typically more conserved from species to species than are promoter sequences.

Probes are generated from tomato genomic DNA using primer-specific amplification (Mullis, 1987; Mullis, et al., 1987). The oligonucleotide primers are selected such that the amplified region includes the entire coding sequence of the tomato E4 or E8 gene. Primers may also be selected to amplify only a selected region of the E4 or E8 gene.

A promotor may also be isolated by (i) selecting first and second oligonucleotide primers corresponding to an upstream and a downstream region, respectively, of an E4 or E8 gene, (ii) amplifying a region of the E4 or E8 gene DNA between the first and second primers to generate probe molecules, (iii) contacting the probe molecules with a plurality of target DNA molecules derived from the genome of a selected fruit-bearing plant under conditions favoring specific hybridization between the probe molecule and a target molecule homologous to the probe molecule.

Alternatively, a probe can be made by isolating restriction-digest fragments containing the sequence of interest from plasmid DNA.

Such a probe is labeled with a detectable moiety to enable subsequent identification of homologous target molecules. Exemplary labeling moieties include radioactive nucleotides, such as $^{32}$P-labeled nucleotides, digoxygenin-labeled nucleotides, biotinylated nucleotides, and the like, available from commercial sources.

In the case of a primer-amplified probe, labeled nucleotides may be directly incorporated into the probe during the amplification process. Probe molecules derived from DNA that has already been isolated, such as restriction-digest fragments from plasmid DNA, are typically end-labeled (Ausubel, et al., 1992).

Target molecules, such as HindIII DNA fragments from the genomes of the above-listed plants, are electrophoresed on a gel, blotted, and immobilized onto a nylon or nitrocellulose filter. Labeled probe molecules are then contacted with the target molecules under conditions favoring specific hybridization between the probe molecules and target molecules homologous to the probe molecules, thereby identifying a target molecule having a DNA sequence homologous (having essentially the same sequence identity) to the tomato E4 or E8 gene, and isolating promoter sequences associated with the target molecule.

Conditions favoring specific hybridization are referred to as moderately-to-highly stringent, and are affected primarily by the salt concentration and temperature of the wash buffer (Ausubel, et al., 1992; Sambrook, et al., 1989). Hybridization conditions are typically classified as moderately stringent, due to the low salt concentration, and are expected to preserve only specific hybridization interactions, allowing the identification and isolation of homologous genes in different plant species.

Following contacting, hybridization, and washing, target molecules with sequences substantially identical to the probe are identified by detecting the label on the probe. The label may be detected directly, for example, as in a radioactive label detected on autoradiograms, or it may be detected with a secondary moiety, for example, fluorescently-labeled streptavidin binding to a biotinylated probe.

Following the identification of plants containing E4 and/or E8 genes, the DNA encoding the genes, including the 5' regulatory regions, may be isolated from the respective species, by screening a genomic DNA library, e.g., a library derived from a fruit-bearing plant.

The library of interest is screened with a probe containing sequences corresponding to the coding sequence of a known E4 gene, such as the tomato E4 gene. The screening is done using known methods (Ausubel, et al., 1992; Sambrook, et al., 1989).

Positive plaques or colonies are isolated, and the insert DNA is sequenced and compared to known E4 sequences. Clones containing inserts with sequences corresponding to genes with substantial sequence identity to tomato E4 are identified and, if necessary, used to obtain additional clones until the promoter region of interest is identified and further isolated. A DNA fragment containing an E4 or E8 promoter, or partial sequence thereof, may be isolated by digesting one of the lambda clones with selected restriction enzymes, e.g., HindIII and SacI. This results in the generation of various fragments which may be purified by electrophoresis on agarose gels. The purified fragments may then be used to obtain the full-length promoter of the target E4 or E8 gene by hybridization using routine techniques know to those of skill in the art.

C. Heterologous Genes

The methods and results described herein demonstrate the ability to provide high level tissue and/or stage specific gene expression in transgenic plants, where expression is regulated by a hybrid E8/E4 hybrid promoter. The E8/E4 hybrid promoter of the present invention includes a region or regions of DNA that regulates transcription of the immediately adjacent (downstream) gene to a specific plant tissue. According to methods of the present invention, heterologous genes are linked to the promoters of the present invention.

Exemplary heterologous genes for the transformation of plants include genes whose products are effective to reduce ethylene biosynthesis in specific tissues of those plants, e.g. the fruits. Some of these genes, including AdoMetase, are discussed above, and include S-adenosylmethionine hydrolase, aminocyclopropane-1-carboxylic acid (ACC) deaminase, ACC oxidase antisense molecule, ACC synthase antisense molecule, ACC oxidase cosuppression molecule, ACC synthase cosuppression molecule.

Other genes of interest that could be used in conjunction with the hybrid E8/E4 promoter include, but are not limited to other ripening modification genes in addition to AdoMetase. Representative examples of such genes include aminocyclopropane-1-carboxylic acid (ACC) deaminase (Klee, et al., 1991; Sheehy, et al., 1991), which degrades precursors of ethylene biosynthesis. Ripening modification can also be achieved through the use of gene inactivation methods. Such methods may employ antisense or cosuppression-effecting genes of the ethylene biosynthetic pathway, e.g., ACC synthase (Sato and Theologis, 1989) and ACC oxidase (Hamilton, et al., 1990).

Additional genes for use in the DNA constructs of the present invention include genes involved in conferring fungal resistance, e.g., the polygalacturonase inhibiting protein, PGIP, from *Phaseolus vulgaris* (Toubart, et al., 1992). Also contemplated are the use of modified forms of plant glucanase, chitinase and other pathogenesis related (PR) genes (Melchers, et al., 1993, 1994; Ponstein, et al., 1994; Woloshuk, et al., 1991). Genes involved in conferring insect resistance may also be incorporated into the DNA constructs of the present invention. The expression of these products would be improved when used with a high-level, fruit-specific promoter such as the hybrid promoter of the present invention.

In addition, antisense or cosuppression genes encoding proteins responsible for degradative processes in the fruit may also be used in conjunction with the promoters of the present invention. Examples of genes of this type include polygalacturonase, cellulase, and pectin methyl esterase (Schuch, 1994). In this way, inhibition of the specific degradation process is targeted only to ripening fruit.

Other gene products which may be useful to express using the hybrid promoters of the present invention include gene products that are effective to modulate; (i) flowering, (ii) flavor (e.g., thaumatin; GENBANK) or color modification (e.g., products that modify lycopene synthesis, for example, arabidopsis lycopene cyclase; GENBANK), (iii) enzymes or other catalytic products such as ribozymes or catalytic antibodies that modify plant cell processes, (iv) ethylene production, such as antisense molecules, enzymes that degrade precursors of ethylene biosynthesis, catalytic products or cosuppression molecules, (v) fungal control, e.g., alternative fungal control genes, (vi) production or levels of plant hormones, (vii) the cell cycle or cell division, and (viii) sucrose accumulation, such as the sucrose phosphate synthase gene (GENBANK) from corn.

Further, it is useful to modulate constitutive expression of some genes in specific tissues, such as expression of any gene that would be deleterious to the fruit if it were expressed constitutively, e.g., genes which encode degradative enzymes that deplete necessary metabolites. Derivatives of the E4/E8 promoter can be used as on/off switches for the tissue and/or stage-specific expression of genes whose expression is under their control.

D. Methods of Transforming Plants

A number of methods, in addition to Agrobacterium-based methods, may be employed to elicit transformation of plant progenitor cells, such as electroporation, microinjection, and microprojectile bombardment. These methods are well known in the art (Comai and Coning, 1993; Klein, et al., 1988; Miki, et al. 1987; Bellini, et al., 1989) and provide the means to introduce selected DNA into plant genomes. Such DNA may include a DNA cassette which consists of a E8/E4 hybrid promoter functionally adjacent to heterologous sequences encoding a desired product, for example, AdoMetase coding sequences.

Representative methods for transforming tomato are described in International PCT Publication WO 95/35387. Representative methods for transforming strawberry or raspberry are described in International PCT Publication WO095/35388. Conventional protocols for transforming Cucumis sp. are described in Fang and Grumet, 1990; Valles and Lasa, 1994; Dong, et al., 1991; Gonsalves, et al., 1994; Yoshioka, et al., 1992; Ayub, et al., 1996.

Transformants and resulting transgenic cells and transgenic plants are identified and evaluated by standard methods (Mathews, et al., 1995).

E. Expression in Heterologous Plant Systems

Experiments performed in support of the present invention demonstrate the versatility of the chimeric gene constructs of the invention (Examples 6, 7). The vector constructs of the present invention can be used for transformation and high level expression of heterologous sequences in transgenic plants. Further, the expression mediated by the promoters described herein appears to be tissue and/or stage-specific even in heterologous plants.

In looking now at experiments carried out in support of the invention, an evaluation of different promoters was conducted. Illustrative plant transformation experiments were carried out in muskmelon (*Cucumis melo*), using SAMase as the exemplary heterologous gene.

Transgenic melons were generated using Agrobacterium-mediated transformation and binary vectors containing a series of fruit and ripening-specific promoters from tomato (Table 2). Exemplary synthetic hybrid promoters containing different fruit-specific and ethylene-responsive promoter domains were prepared (i.e., the long and short E8/E4 hybrid promoters) to determine their ability to enhance fruit and ripening specific gene expression.

Transgenic melons containing the SAMase gene were identified using PCR. Several transgenic events for each of the binary vectors were analyzed using Western blotting techniques to determine expression of the SAMase gene in ripening melon fruit.

Figure 6:
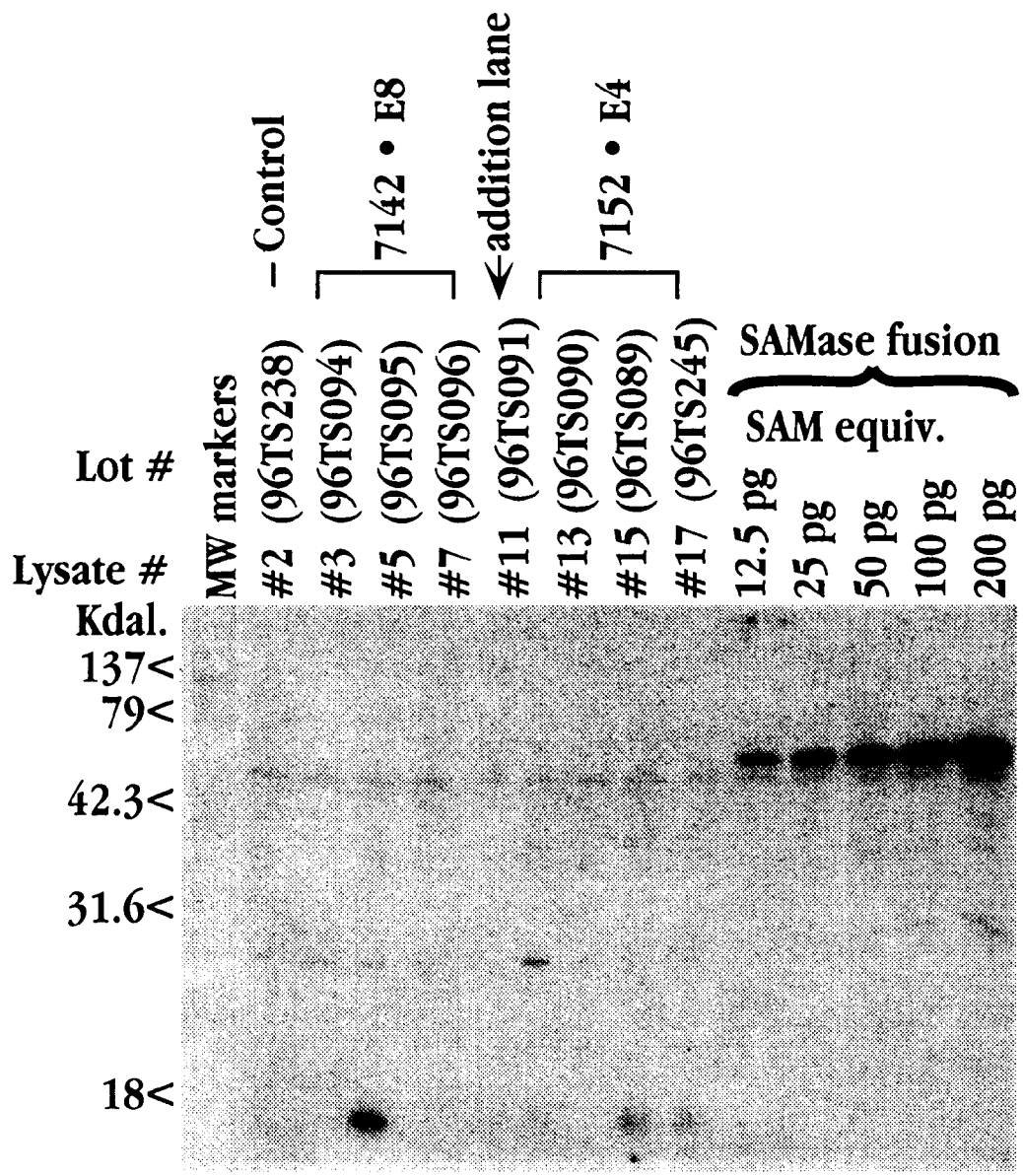
FIG. 6 is a computer-generated image of a Western blot indicating SAMase expression in ripe melons transformed with binary vectors pAG7142 (tomato E4::SAMase) and pAG7152 (tomato E8::SAMase)
Figure 7:
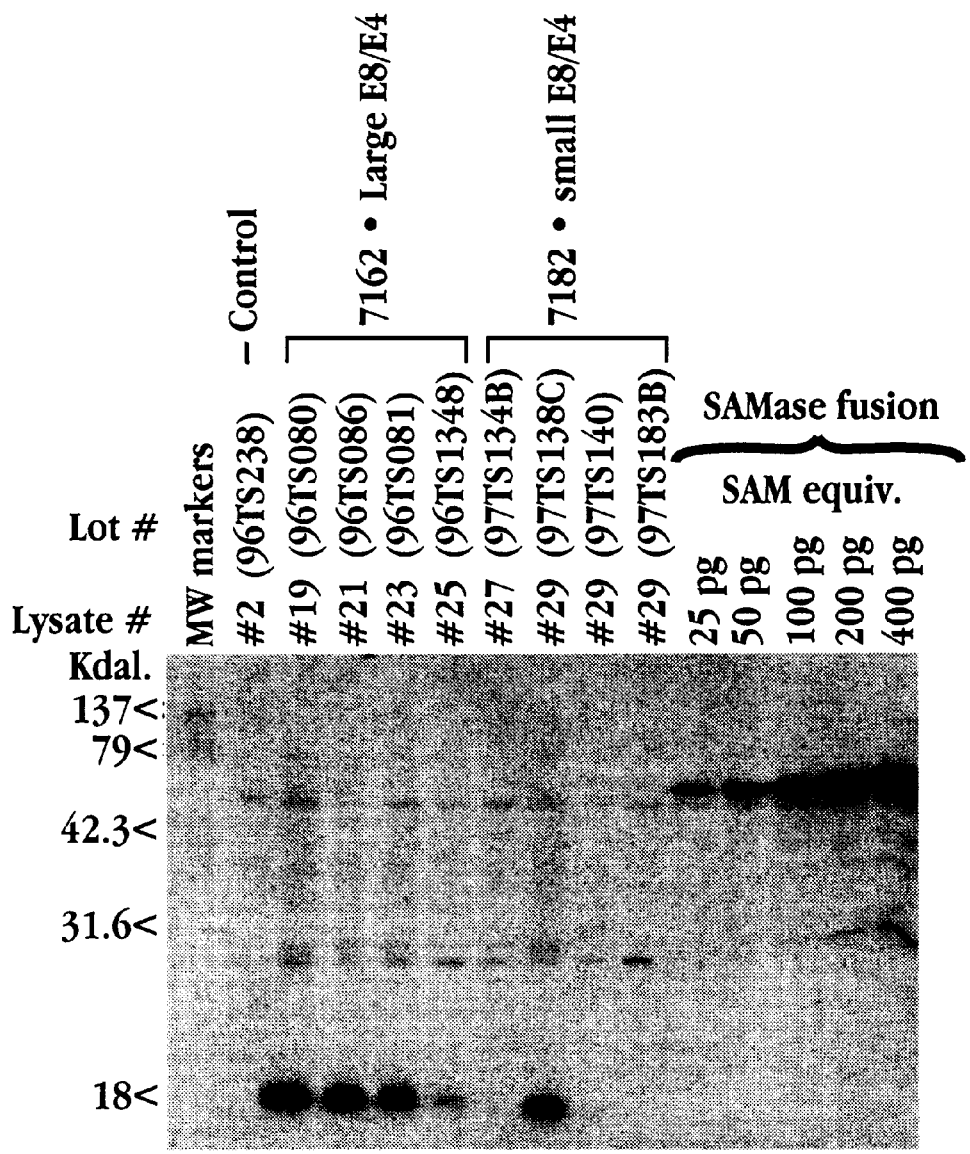
FIG. 7 is a computer-generated image of a Western blot indicating SAMase expression in ripe melons transformed with binary vectors pAG7162 (long or large tomato E8-E4::SAMase) and pAG7182 (short or small tomato E8-E4::SAMase)

FIGS. 6 and 7 indicate that neither the E8 nor the E4 promoters alone (FIG. 6) are equivalent to the E8/E4 hybrid promoters, in particular the long E8/E4 hybrid (FIG. 7), in their ability to drive expression of SAMase in ripening melon fruit. While expression in the E4 and E8 driven constructs was observed to be weak-to-moderate, expression levels for the corresponding hybrid promoters was significantly greater, as determined by the intensity of the 17 kd AdoMetase band on the blot.

To further confirm and compare expression of the introduced transgenes, representative ethylene biosynthesis profiles were determined over a 4 day period for melon samples transformed with each of the representative constructs presented in Table 2.

Figure 8:
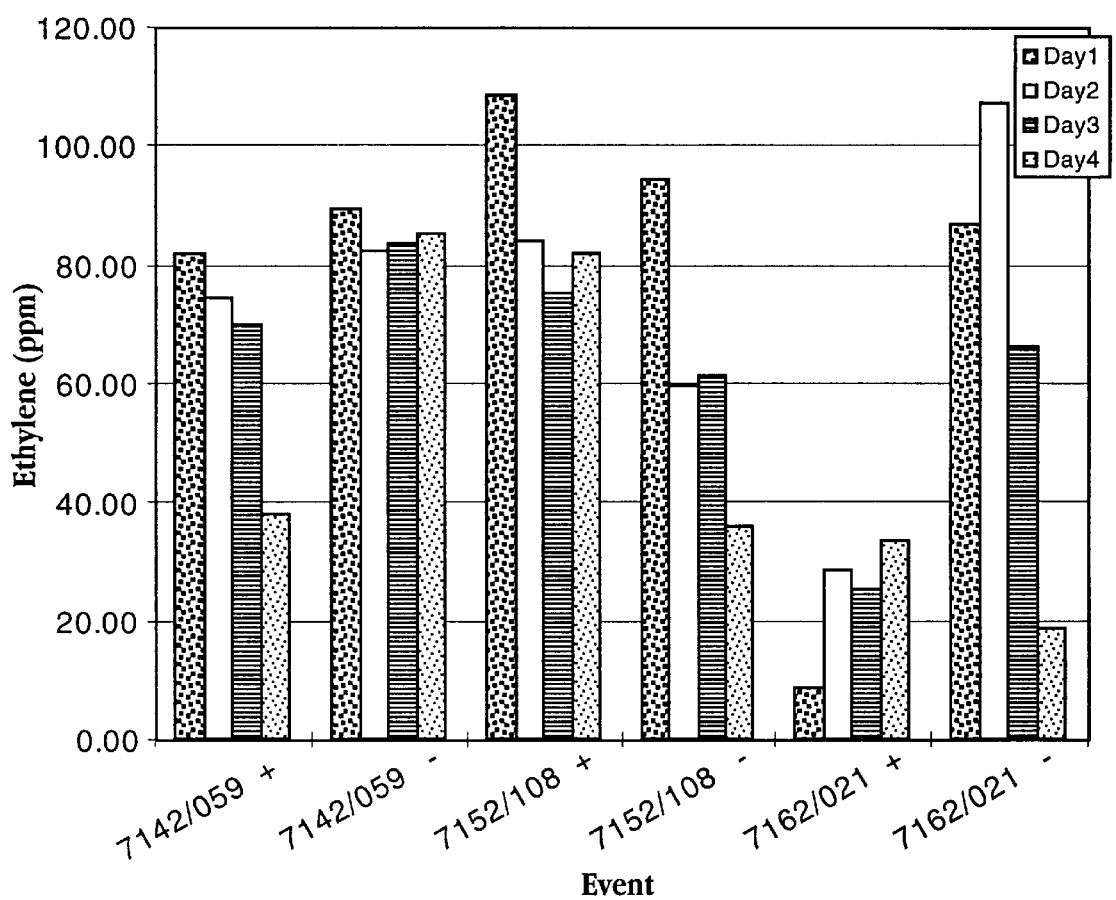
FIG. 8 is a bar graph representing ethylene biosynthesis profiles over a 4-day period for three different transgenic events (pAG-7142 and control; pAG-7152 and control; and pAG-7162 and control)

Ethylene synthesis from the three different events (pAG-7142, pAG-7152, pAG-7162) are shown in FIG. 8, where entries followed by a (–) designation represent negative controls. In looking now at the results presented in FIG. 8, the pAG-7162-derived event (long E8/E4 hybrid promoter) is clearly reduced in its ability to produce ethylene during ripening, to an extent significantly greater than that of either of the E4 or E8-promoter driven events. Reduced ethylene synthesis and delayed ripening correlated with SAMase gene expression levels determined by Western blotting.

The long E8/E4 hybrid promoter-driven events demonstrate reduced ethylene biosynthesis, when compared to both the negative controls and to the other non-hybrid promoter-driven events. This is an indication of the greater expression activity of the hybrid promoter of the invention when compared to various non-hybrid promoters derived from different types of plant genes.

The use of the hybrid E4/E8 promoters cannot be considered limited to melon and tomato. The constructs and methods of the present invention are applicable to all higher plants, particularly fruits.

As demonstrated herein, the E4/E8 hybrid promoter sequences may be isolated from a type of plant other than the plant to be transformed. This is exemplified by the activity of an E4/E8 hybrid promoter composed of tomato-derived sequences which is effective to express a heterologous gene, e.g., the SAMase gene in muskmelon. Alternatively, the E4/E8 hybrid promoter sequences may be isolated from the same type of plant as that which is transformed by a vector which contains an E4/E8 hybrid promoter and a heterologous coding sequence, e.g. the SAMase gene. For example, a raspberry E4/E8 hybrid promoter may be operably linked to a heterologous gene, such as the SAMase gene, and used to transform raspberries.

The following examples illustrate, but in no way are intended to limit the scope of the present invention.

Materials and Methods

DNA Plasmids and Agrobacterium Binary Vector Constrictions

Biological reagents were typically obtained from the following vendors: 5' to 3' Prime, Boulder, Colo.; New England Biolabs, Beverly, Mass.; Gibco/BRL, Gaithersburg, Md.; Promega, Madison, Wis.; Clontech, Palo Alto, Calif.; and Operon, Alameda, Calif.

Standard recombinant DNA techniques were employed in all constructions (Adams and Yang, 1977; Ausubel, et al., 1992; Hooykaas and Schilperoot 1985; Sambrook, et al., 1989.

EXAMPLE 1

Long E8/E4 Hybrid Promoter (2.8 kb) and Preparation of Intermediate Vector pAG-1762

A. Construction of Intermediate Vector pAG-1762

An intermediate vector, pAG-1762, which assembled all of the necessary elements into a moveable cassette was prepared as follows.

To obtain a portion of the tomato E8 promoter for use in preparing a hybrid promoter, a plasmid containing the 2.0 kb tomato E8 promoter, pAG-1742, was digested with XbaI and BamHI using standard molecular biology protocols (Sambrook, et al., 1989). The sequence of the 5' flanking region of the tomato E8 gene corresponding to 1 to −1098 and −2181 to −1098 has been previously described by Deikman, et al, 1988 and Deikman, et al., 1992, respectively.

Figure 4:
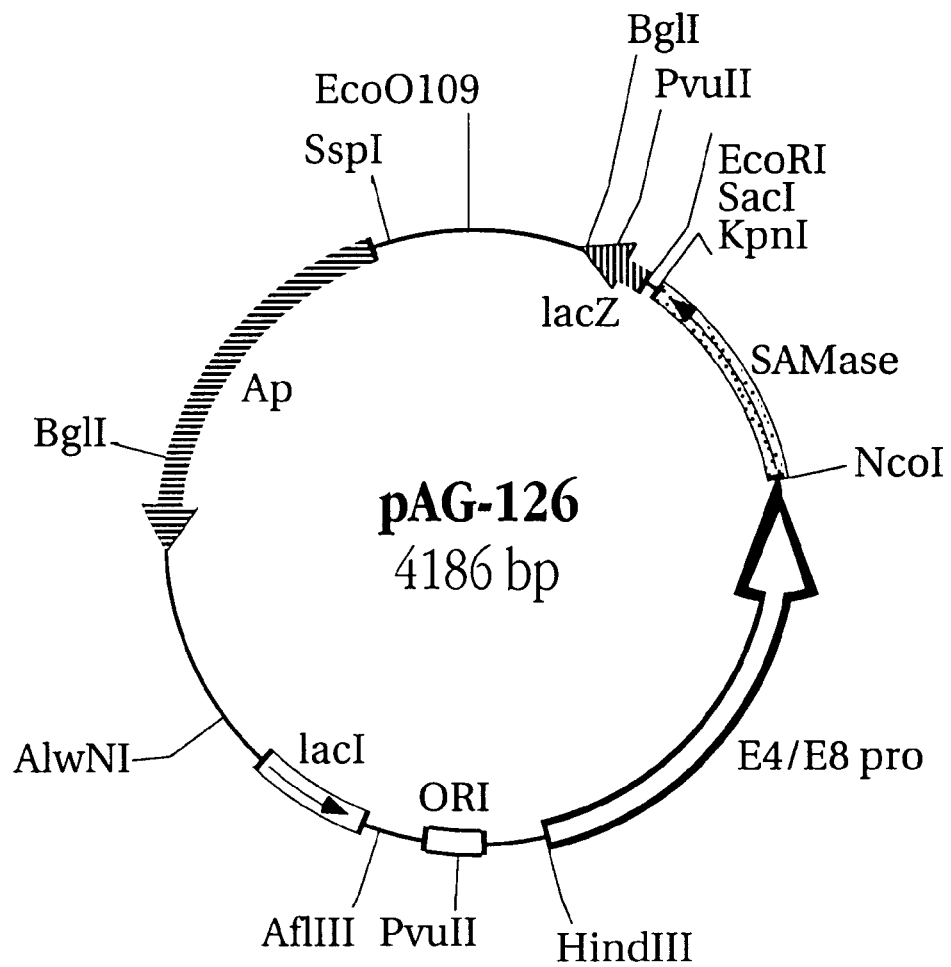
FIG. 4 presents a schematic representation of the details of the construction of an intermediate transfer vector pAG-126 (4186 bp)

A lambda genomic library from tomato was screened by standard methods with a tomato E8 gene probe based on sequences described by Diekman et al. A lambda clone which hybridized to the probe was identified, plaque purified and sequenced. The E8 genomic clone was used as a source of the HindIII fragment that is the approximately −2257 to −1103 bp upstream region of the hybrid E8/E4 promoter of the present invention, corresponding to nucleotides 1–1155 of SEQ ID NO:7. This fragment was inserted 5' of the approximately 1122 bp E8 promoter in pAG-5321 at the HindIII and XbaI sites (FIG. 4).

The DNA sequence of the −2257 to −1103 base pair region is presented herein as nucleotides 1 to 1160 of FIGS. 2A and 2B. Following digestion, the excised tomato E8 promoter fragment was purified by electro-elution after agarose gel electrophoresis. The purified fragment was determined to contain the upstream sequence of the E8 promoter corresponding to nucleotides −2257 to −1098. The sequence corresponding to nucleotides −2257 to −1098 of the tomato E8 promoter is presented as nucleotides 1 to 1160 of SEQ ID NO:1 and 7.

To isolate a full-length E4 promoter for use in constructing a hybrid promoter, a 10.6 kb fragment containing the tomato E4 promoter was excised from a second plasmid, pAG-1752, by treatment with XbaI and BamHI. The sequence of the tomato E4 promoter has been published (Cordes, et al., 1989), and the DNA sequence of the minus 1150 to plus 16 base pair region is presented as nucleotides 271 to 1437 of SEQ ID NO:8, which encompasses the full E4 gene.

The excised 10.6 kb fragment contained a tomato E4 promoter:SAMase construct. The sequence of the SAMase gene is described in U.S. Pat. No. 5,589,623. The cloning and isolation of the SAMase gene is described in International Publication No. WO 95/35387. Also described therein are representative methods for isolating and characterizing a tomato E4 and/or E8 promoter, and details for preparing vector constructs of the type employed herein. The excised fragment, which contained the necessary sequences for bacterial selection and replication, was purified on agarose gel.

These two fragments were combined following the ligation protocol of Gibco/BRL to produce plasmid pAG-1762. This plasmid is shown schematically in FIG. 1.

EXAMPLE 2

Preparation of Binary Vector, pAG-7162
Containing Long E8/E4 Hybrid Promoter

The promoter/gene cassette from the intermediate vector, pAG-1762, was transferred into a binary vector as follows.

Plasmid pAG-1762 (Example 1) was digested with HindIII and KpnI, resulting in a 2.8 kb fragment containing the long E8/E4 promoter (FIGS. 2A, 2B; SEQ ID No:1) and SAMase. The excised fragment was gel purified by electrophoresis on agarose.

A second plasmid, pAG-7142 (FIG. 12) was digested with HindIII and KpnI to provide a 12 kb fragment containing a terminator sequence and a selectable marker cassette (i.e., the nptII kanamycin resistance gene driven by the raspberry E4 promoter) as well as the necessary sequences for bacterial selection and replication. The isolation, characterization, and sequence of the raspberry E4 (RE4) promoter, along with illustrative constructs describing the use of this promoter, are described in International PCT Publication WO 95/35388. The 12 kb fragment was purified by electrophoresis on agarose.

Figure 3:
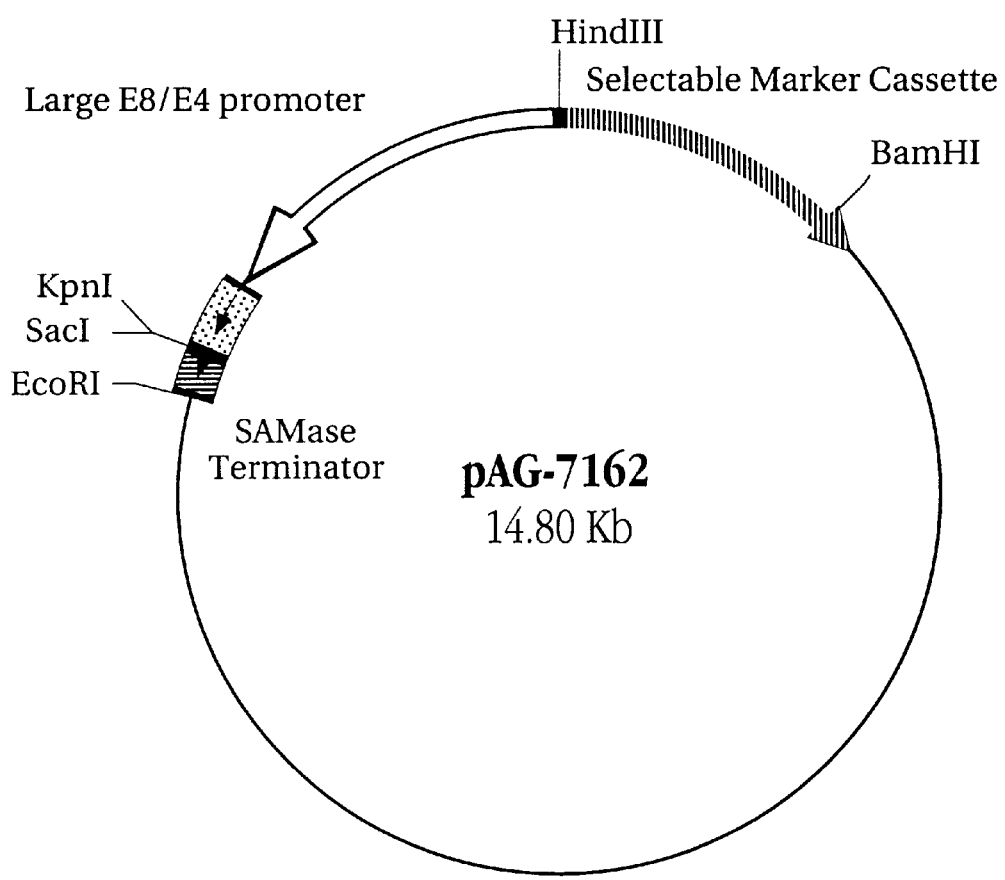
FIG. 3 presents a schematic representation of the details of the construction of an intermediate vector pAG-7162 (14.80 kb)

The purified 2.8 kb fragment containing the long E8/E4 promoter::SAMase construct was then ligated to the above-described purified 12 kb fragment to form plasmid pAG-7162, as illustrated schematically in FIG. 3.

EXAMPLE 3

Preparation of a Short E8/E4 Hybrid Promoter and an Intermediate Transfer Vector, pAG-126

An intermediate vector combining truncated polynucleotide segments derived from the tomato E4 and E8 gene promoters to form a short E8/E4 hybrid promoter fused to the coding sequence for SAMase, was prepared as follows.

A tomato E4 promoter segment corresponding to nucleotides −315 to +16 was isolated from tomato DNA using PCR. In a similar fashion, PCR primers were designed to amplify a segment of the E8 promoter from −1529 to −847. The oligonucleotide primers were designed to incorporate restriction endonuclease sites at the ends of the amplified promoter fragments, for ready subcloning. The design of the primers was based on the published sequences of the tomato E8 and E4 genes as described above, using OLIGO version 5.0 for MacIntosh, a multi-functional sequence analysis program from National Biosciences, Inc. (Plymouth, Minn.).

TABLE 1

| Primer | Sequence | ID No. |
|---|---|---|
| E4promod5 | 5'-ACT CTT CCA CAC TTT TCC CTC TA-3'<br>underline = EarI site | SEQ ID No: 2 |
| E4promod3 | 5'-CCC ATG GCT CAA TCT CTA AT-3'<br>underline = NcoI site | SEQ ID No: 3 |

TABLE 1-continued

| Primer | Sequence | ID No. |
|---|---|---|
| E8promod5 | 5'C<u>AA GCT TAA</u> AAT GTA CGA TGA GAG-3'<br>underline = *Hind*III site | SEQ ID No: 4 |
| E8promodLo | 5'-AGT GTC <u>GAA GAG</u> GAC TAA ACC CGA AAA T-3'<br>underline = *Ear*I site | SEQ ID No:5 |

PCR was performed according to the manufacturer's procedure using Amplitaq (Perkin Elmer, Applied Biosystems Division, Foster City, Calif.), PCR buffer, tomato genomic DNA, and either pair of the above primers, employing the following (hot start) conditions:

1 cycle of 97° C. for 5 minutes following addition of Amplitaq;

2 cycles of 97° C. for 1 minute, 52° C. for 1 minute and 72° C. for 1 minute;

25 cycles of 94° C. for 1 minute, 52° C. for 1 minute and 72° C. for 1 minute;

1 cycle of 72° C. for 5 minutes; followed by cooling to 5° C.

The PCR-amplified fragments were each digested separately with EarI. These two amplified fragments were then combined in a ligation reaction following conventional protocol (Gibco/BRL) utilizing ligase and buffer obtained from Gibco/BRL. The ligase reaction products were purified and the recovered DNA was subjected to digestion with restriction enzymes NcoI and HindIII (New England Biolabs, Beverly, Mass.).

The resulting short E8\E4 promoter fragment was then purified and ligated into a suitable plasmid vector. The vector, which contained the SAMase gene, was digested with HindIII and NcoI in order to orient the hybrid promoter immediately upstream of the SAMase gene, with both the promoter and gene positioned in the same 5' to 3' direction.

The resulting intermediate plasmid containing a short E8\E hybrid promoter::SAMase construct was designated pAG-126 and is presented in FIG. 4.

EXAMPLE 4

Preparation of a Binary Vector Containing a Short E8/E4 Hybrid Promoter

The above-described promoter/gene cassette was transferred into a binary vector as follows.

Plasmid pAG-126 was digested with HindIII and KpnI to produce a 1.5 kb fragment containing the E8/E4 hybrid promoter coupled to the SAMase gene. The excised fragment was gel purified.

A binary plasmid vector, pAG-7142, containing a selectable marker gene cassette and a terminator sequence oriented downstream of the SAMase gene, was similarly treated with HindIII and KpnI. A schematic representation of vector pAG-7142 is presented as FIG. 12.

Figure 5:
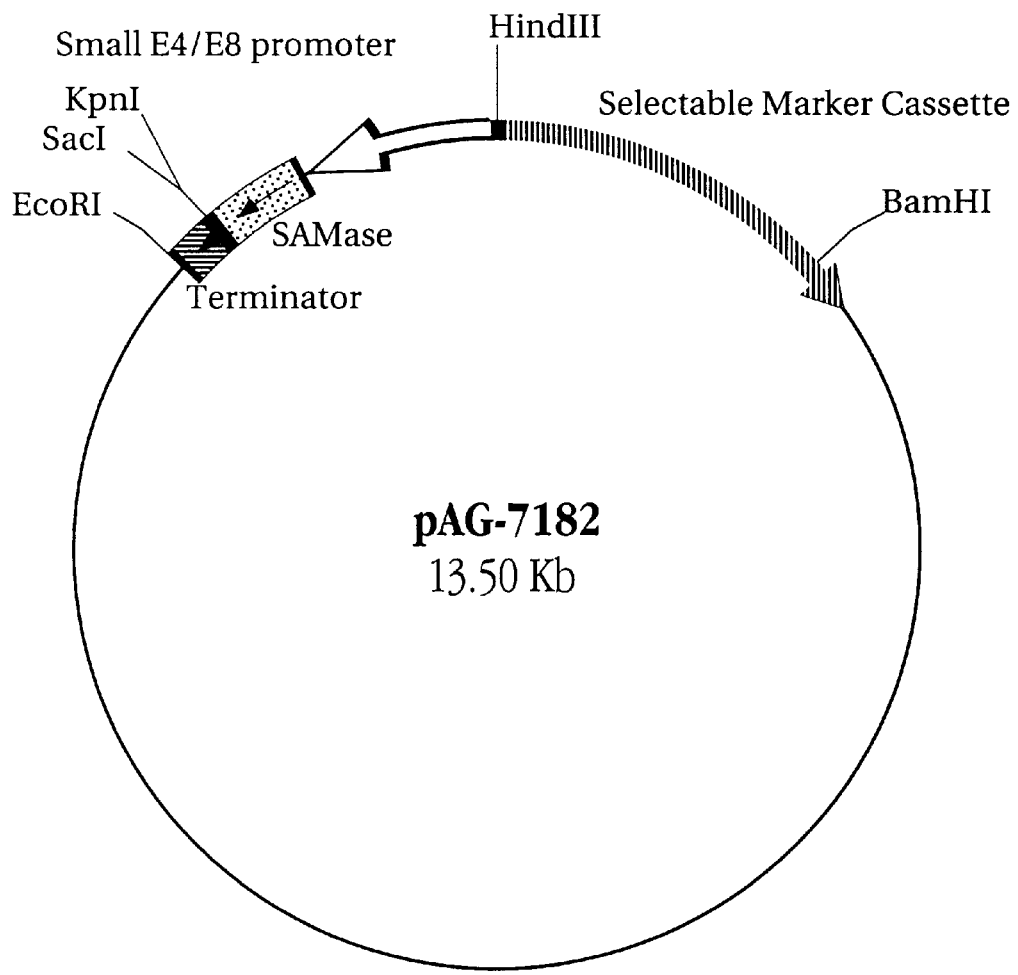
FIG. 5 presents a schematic representation of plasmid pAG-7182 (13.50 kb)

The 1.5 kb short E8/E4 hybrid promoter::SAMase fragment was then ligated to the binary vector to produce plasmid, pAG-7182, as shown in FIG. 5.

EXAMPLE 5

A. Construction of Binary Vectors Containing Known Promoters

Figure 9:
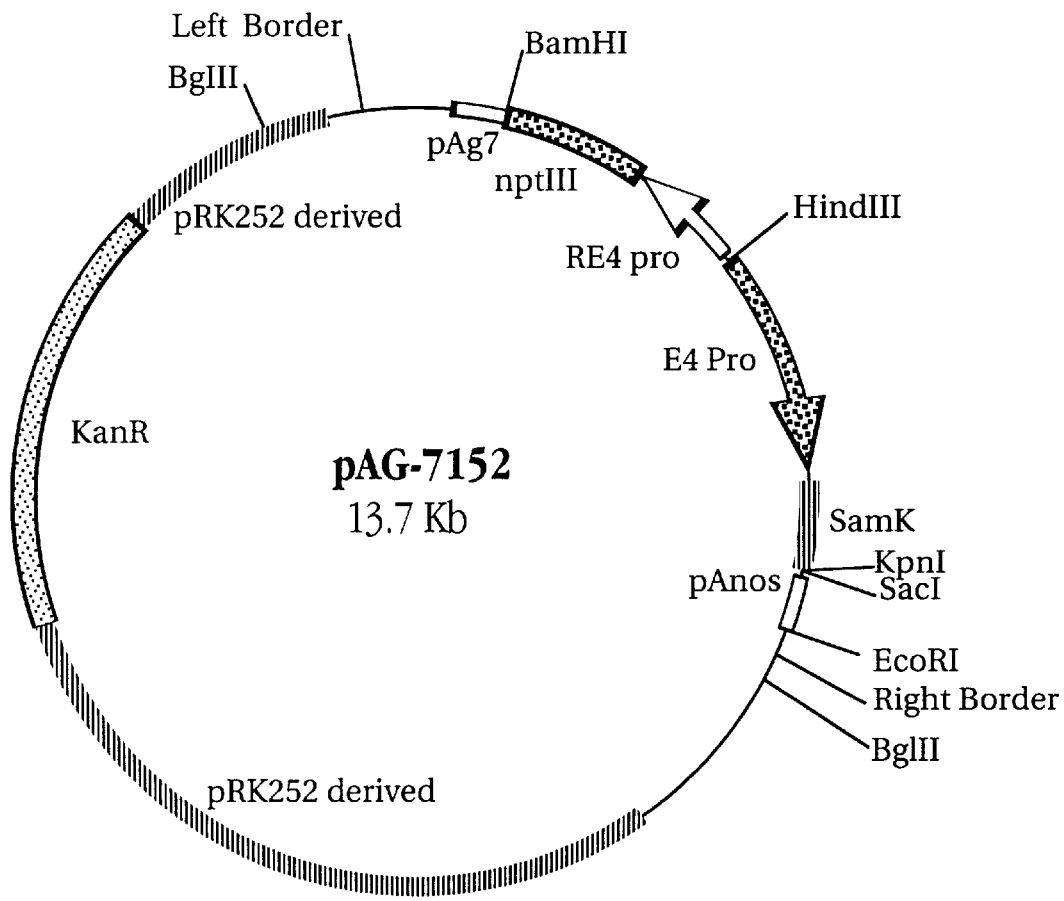
FIG. 9 is a schematic representation of the construction of vector pAG-7152 containing the tomato E4 promoter (13.7 kb)
Figure 12:
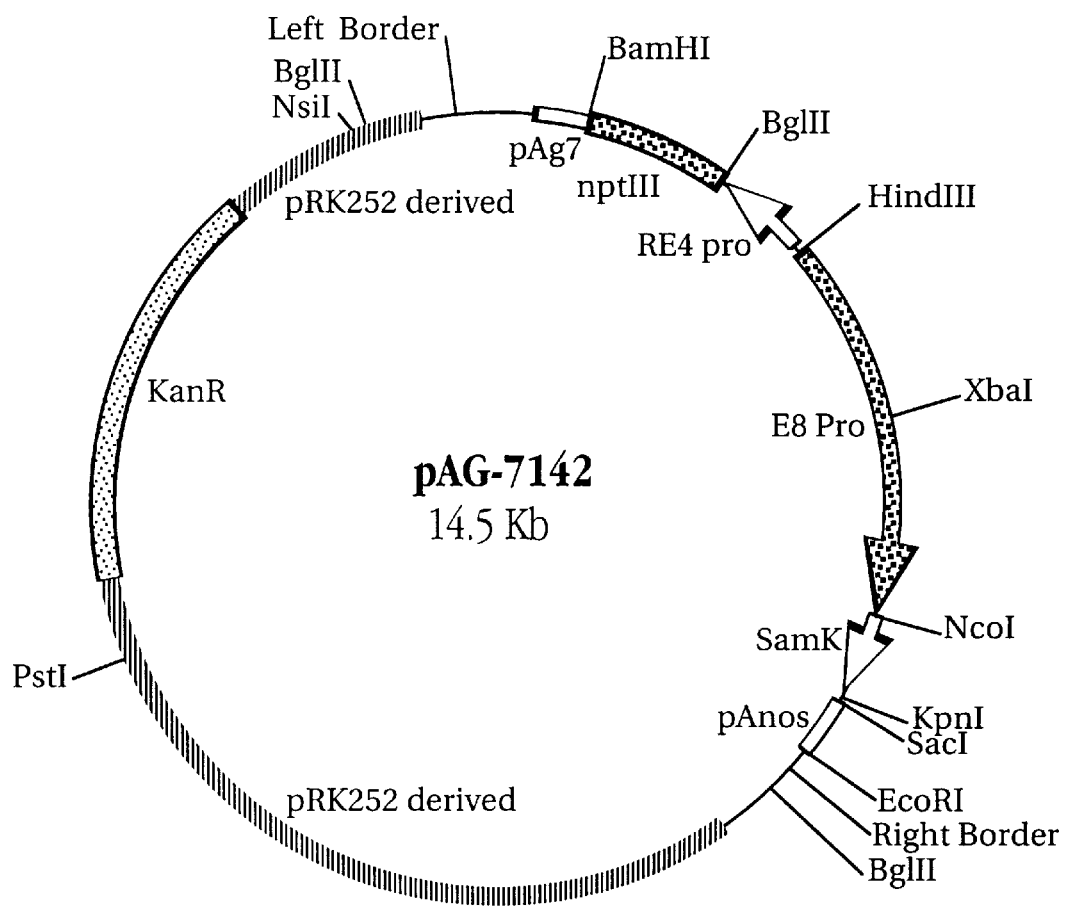
FIG. 12 is a schematic representation of the construction of vector pAG-7142 containing the tomato E8 promoter (14.5 kb).

Binary vectors pAG-7142 (E4::SAMase) and pAG-7152 (E8::SAMase) were constructed following conventional protocols. Circular restriction maps of these plasmid vectors are shown in FIGS. 12 and 9, respectively. The elements contained in each of the vectors were identical, with the exception of the promoter driving expression of SAMase.

B. Transformation of *Cucumis Melo* (Muskmelon)

Cotyledon explants of a commercial cantaloupe variety were transformed according to known methods (Fang and Grumet, 1990; Valles and Lasa, 1994; Dong, et al., 1991; Gonsalves, et al., 1994; Yoshioka, et al., 1992; Ayub, et al., 1996).

The disarmed Agrobacterium strain EHA105 (Hood, et al., 1993) was used to introduce the above-described binary vectors into plants. The disarmed Agrobacterium strain was cocultivated with melon cotyledon tissue explants. Primary transformants were selected on the basis of their capacity to regenerate and develop roots on media containing the antibiotic, kanamycin.

The presence of the SAMase gene in the putative transgenic plants was confirmed using the polymerase chain reaction and primers specific for the SAMase gene.

Primary transgenic plants were grown in a greenhouse. Individual melon fruit were harvested at a stage when the fruit had initiated the process of abscission. Harvested fruit were stored under refrigeration for 7 days. Samples were then frozen at −70° C. for storage prior to gene expression studies.

EXAMPLE 6

Western Blot Analysis of SAMase Gene Expression

Protein lysates were prepared from the melon pericarp fruit tissue of each sample and were free of any rind tissue. Using liquid nitrogen and a mortar and pestle, one gram tissue samples were ground to a fine powder, mixed with Laemmli SDS sample buffer (Laemmli, 1970) and heated at 95–100° C. to denature the proteins.

Protein concentrations were determined by precipitating the proteins from the melon lysate with trichloroacetic acid, resolubilizing the proteins, followed by a quantification of protein concentration using Pierce's BCA (bicinchoninic acid) assay kit, according to the manufacturer's instructions. Sodium dodecyl sulphate polyacrylamide gel electrophoresis (SDS PAGE) was performed using Laemmli's denaturing (SDS) discontinuous gel electrophoresis method (Laemmli, 1970).

Proteins resolved by SDS PAGE were transblotted on to Millipore's Immobilion-P PVDF membrane in Tris-glycine/15% methanol buffer at 100 volts for 2 hours. The membranes were then treated with 5% (w/v) powdered milk in phosphate buffered saline (PBS) containing Tween 20 for 2 hours at room temperature.

The primary antibody treatment was performed using 1 µg/ml of an anti-SAMase mouse monoclonal antibody in 3.5% powdered milk/PBS-Tween 20 for 2 hours at room temperature. The secondary antibody, a horseradish peroxidase-labeled goat anti-mouse IgG+IgM(H+L) polyclonal antibody (Kirkegaard and Perry Laboratories, Inc., Gaithersberg, Md.), was used to treat the membrane at 0.1 μg/ml in 3.5% powdered milk/PBS-Tween 20 for 2 hours at room temperature. Membrane bound antibody was detected using NEN/DuPont's Renaissance chemiluminescence reagent in a 1 minute incubation as per the manufacturer's instructions. The blot was then exposed to Kodak BioMax MR X-ray film for at least one hour.

TABLE 2

Summary of Agrobacterium Vectors Used to Transform Melon

| Construct ID # | Promoter::SAMase | Promoter::Selectable Marker |
|---|---|---|
| pAG-7142 | Tomato E8::SAMase | RE4::nptII |
| pAG-7152 | Tomato E4::SAMase | RE4::nptII |
| pAG-7162 | Long E8/E4::SAMase | RE4::nptII |
| pAG-7182 | Short E8/E4::SAMase | RE4::nptII |

All of the binary vector constructs are identical with the exception of the promoter controlling expression of the exemplary SAMase gene.

Several transgenic events for each of the binary vectors were analyzed using Western blots to determine expression of the SAMase gene in ripening melon fruit.

FIGS. 6 and 7 indicate that neither the E8 nor the E4 promoters alone are equivalent to the E8/E4 hybrid promoters, in particular the long E8/E4 hybrid, in their ability to drive expression of SAMase in ripening melon fruit.

EXAMPLE 7
Ethylene Production in Melon Transformants

Representative ethylene biosynthesis profiles were determined over a 4 day period. At day zero, transformed melon was at a physiological ripening stage known as ¼ slip. "Slip", in melon ripening terminology, refers to the abscission of the fruit from the peduncle of stem region which attaches the melon to the vine. Thus, ¼ slip signifies the initiation of the ripening process.

The assay for ethylene evolution in transgenic melon fruit is performed by placing a rubber cup over the stem end of individual fruit and sampling 0.25 ml aliquots for gas chromatographic analysis after approximately four hours (Ayub, et al., 1996). A Hewlett Packard 6890 (Hewlett Packard, Palo Alto, Calif.) gas chromatograph with a flame ionization detector and a 6 ft Haysep-D column was used for ethylene measurements. This system, when utilized in combination with an HP Vectra computer and the current version of "CHEMSTATION" (Hewlett Packard) allows measurement of ethylene concentrations as low as 0.1 ppm.

Ethylene synthesis from the three different events (pAG-7142, pAG-7152, pAG-7162) are shown in FIG. 8, where entries followed by a (−) designation represent negative controls. The results are typical of other transgenic events that have been analyzed to date.

In looking now at the results presented in FIG. 8, the pAG-7162-derived event (long E8/E4 hybrid promoter) is clearly reduced in its ability to produce ethylene during ripening, to an extent significantly greater than that of either of the E4 or E8-promoter driven events. The long E8/E4 hybrid promoter-driven events demonstrate reduced ethylene biosynthesis, when compared to both the negative controls and to the other non-hybrid promoter-driven events.

What is claimed is:

1. A chimeric gene comprising a tomato E4/E8 hybrid promoter comprising, in the 5' to 3' direction:
   a first nucleotide segment consisting of nucleotides 1 to 1156 of the tomato E8 gene promoter sequence presented as SEQ ID NO:7 fused to a second nucleotide segment consisting of nucleotides 271 to 1437 of the tomato E4 gene promoter sequence presented as SEQ ID NO:8.

2. A chimeric gene comprising a tomato E4/E8 hybrid promoter comprising, in the 5' to 3 direction:
   a first nucleotide segment comprising nucleotides 729 to 1411 of the tomato E8 gene promoter sequence presented as SEQ ID NO:7 fused to a second nucleotide segment comprising nucleotides 1107 to 1437 of the tomato E4 gene promoter sequence presented as SEQ ID NO:8.

3. A chimeric gene comprising a tomato E4/E8 hybrid promoter comprising, in the 5' to 3' direction:
   a first nucleotide segment consisting of nucleotides 729 to 1411 of the tomato E8 gene promoter sequence presented as SEQ ID NO:7 fused to a second nucleotide segment consisting of nucleotides 1107 to 1437 of the tomato E4 gene promoter sequence presented as SEQ ID NO:8.

4. The chimeric gene according to claim 1, 2, or 3, further comprising a heterologous DNA coding sequence operably linked to said hybrid promoter.

5. The chimeric gene according to claim 4, wherein said hybrid promoter drives fruit-specific expression of the heterologous DNA coding sequence in a plant.

6. The chimeric gene according to claim 5, wherein said heterologous DNA coding sequence encodes S-adenosylmethionine hydrolase (SAMase).

7. A vector comprising the chimeric gene according to claim 1, 2, or 3.

8. A plant cell comprising the chimeric gene according to any one of claims 1, 2, or 3.

9. A method of producing a transgenic fruit-bearing plant characterized by reduced ethylene production during fruit ripening, comprising the steps of:

(i) introducing into progenitor cells of said plant, a DNA construct comprising:
   a hybrid E4/E8 promoter sequence comprising in the 5' to 3' direction a first nucleotide segment comprising nucleotides 729 to 1411 of the tomato E8 gene promoter sequence presented as SEQ ID NO:7 fused to a second nucleotide segment comprising nucleotides 1107 to 1437 of the tomato E4 gene promoter sequence presented as SEQ ID NO:8; and
   a heterologous DNA sequence which encodes a a protein which reduces ethylene biosynthesis operably linked to the E4/E8 promoter, to produce transformed progenitor plant cells; and (ii) regenerating the transgenic fruit-bearing plant from the transformed progenitor cells, wherein fruit of the transgenic fruit-bearing plant have reduced ethylene production during fruit ripening relative to fruit of a non-transformed plant.

10. The method according to claim 9, wherein expression of the heterologous DNA sequence in the fruit of said transgenic fruit-bearing plant results in delayed ripening of the fruit relative to fruit from a non-transformed plant.

11. The method according to claim 9, wherein the heterologous DNA sequence encodes S-adenosylmethionine hydrolase (SAMase).

12. The method according to claim 10, wherein the plant is a Cucumis sp.

13. The method according to claim 10, wherein said E4/E8 hybrid promoter comprises a first nucleotide segment consisting of nucleotides 1 to 1156 of the tomato E8 gene promoter sequence presented as SEQ ID NO:7 fused to a second nucleotide segment consisting of nucleotides 271 to 1437 of the tomato E4 gene promoter sequence presented as SEQ ID NO:8.

14. The method according to claim 10, wherein said E4/E8 hybrid promoter comprises a first nucleotide segment consisting of nucleotides 729 to 1411 of the tomato E8 gene promoter sequence presented as SEQ ID NO:7 fused to a second nucleotide segment consisting of nucleotides 1107 to 1437 of the tomato E4 gene promoter sequence presented as SEQ ID NO:8.

* * * * *

SEQUENCE LISTING

```
<160> NUMBER OF SEQ ID NOS: 10

<210> SEQ ID NO 1
<211> LENGTH: 2327
<212> TYPE: DNA
<213> ORGANISM: Artificial Sequence
<220> FEATURE:
<221> NAME/KEY: misc_feature
<222> LOCATION: (1)...(2327)
<223> OTHER INFORMATION: n = A,T,C or G
<220> FEATURE:
<221> NAME/KEY: promoter
<222> LOCATION: (1)...(2327)
<223> OTHER INFORMATION: synthetic DNA promoter sequence

<400> SEQUENCE: 1
aagctttaat tggttgagat tgaacgtaat tcaaattatt ctgagcccaa acccttaaaa      60
ttctaggcgg ttatctttgt ttgaattcat ttttgacatc cctaatgata ttgttcacgt     120
aattaagttt tgtggaagtg agagagtcca attttgataa gaaaagagtc agaaaacgta     180
atattttaaa agtctaaatc tttctacaaa taagagcaaa tttatttatt ttttaatcca     240
ataaatatta atggaggaca aattcaattc acttggttgt aaaataaact taaaccaata     300
accaaagavc taataaatct gaagtggaat tattaaggat aatgtacata gacaatgaag     360 aataatagg ttcgatgaat taataataat taaggatgtt acaatcatca tgtgccaagt      420
atatacacaa tattctatgg gatttataat ttcgttactt cacttaactt ttgcgtaaat     480
aaaacgaatt atctgatatt ttataataaa acagttaatt aagaaccatc attttaaca     540 acatagatat attatttcta atagtttaat gatacttta aatctttaa attttatgtt       600
```

-continued

```
tcttttagaa aataaaaatt caaaaaaatt aaatatattt acaaaaacta caatcaaaca       660
caacttcata tattaaaagc aaaatatatt ttgaaaattt caagtgtcct aacaaataag       720
acaagaggaa aatgtacgat gagagacata aagagaacta ataattgagg agtcctataa      780
tatataataa agtttattag taaacttaat tattaaggac tcctaaaata tatgatagga      840
gaaaatgaat ggtgagagat attggaaaac ttaataatta aggatnttaa aatatatggt     900
aaaagatagg caaagtatcc attatcccct tttaacttga agtctaccta ggcgcatgtg     960
aaaggttgat tttttgtcac gtcatatagc tataacgtaa aaaaagaaag taaaattttt    1020 aattttttt aatatatgac atattttaaa cgaaatatag gacaaaatgt aaatgaatag      1080
taaaggaaac aaagattaat acttactttg taagaattta agataaattt aaaatttaat   1140
agatcaactt tacgttaaag taaacttggg tgggtcaaga cccaactcga tttctgttca    1200
acccatttta atatttctat tttcaaccta acccgctcat ttgatacccc tacaaatatc    1260
atatttgtgt gtgaaatatt ttttgggctg agagagagag ccccgagggg agtggagggg    1320
tggggtgggg agagagagcg agaaagagtg gagagagaaa tttgatatga aatcctacat    1380
atattacaga ttgtaatgtt ctaaactata acgatttgtc ataaacacat atcatggatt    1440 tgtcttttg tgtaattttc ccaattgtaa ataggacttc gttatttgaa acttgaaagt    1500
gaagtcacat agattaagta caaacattaa ttaaagaccg tggtggaatg ataaatattt    1560
atttatcttt aattagttat ttttttggga gctctttatt ccaatgtgag acttttgcga    1620
catatattca aatttaatcg aatcacaata tgtattagat tgataaaaaa ataatttttt    1680
tacaatgtta gttgagactc ataacttact gcctattggt aatctatgac tcctaattcc    1740
ttaattattt aaatatatca tcttgatcgt taacaaagta atttcgaaag accacgagta    1800
agaagacaaa cgagaatacc aaaaaattca aaaatttaat gtgatttggt caatcgatct    1860
acgtccataa aggagatgag taatctacta taaatatgag agtacaaaat acagagagaa    1920
acaacctcaa ctaattcact cggaatacat gagaagttca cacaagtgat aacgtatcaa    1980
acttgtgacc cacactttc cctctaacca aagctcttaa aactatattg tgaatgctga    2040
ttaagttaaa cgaaacagtc ctaaatcttt tccgtcctat gagaaacaag attaatcaat    2100 tcacaattt tttaaaaga aaaacctgta agaaatttag gcaaacaaaa cctaacacaa      2160
gtttgttttt gttttactag ccaacaagaa attcaaatgg caaatgtata acgcatctta    2220
gctaattata tgaccagatt cagattaata tacatcttca cccatgcaat ccatttctat    2280
ataaagaaac atacacgaac ttgatattat tagagattga gccatgg                  2327
```

<210> SEQ ID NO 2
<211> LENGTH: 23
<212> TYPE: DNA
<213> ORGANISM: Artificial Sequence
<220> FEATURE:
<221> NAME/KEY: primer_bind
<222> LOCATION: (1)...(23)
<223> OTHER INFORMATION: synthetic oligonucleotide

<400> SEQUENCE: 2
actcttccac acttttccct cta                                              23

<210> SEQ ID NO 3
<211> LENGTH: 20
<212> TYPE: DNA
<213> ORGANISM: Artificial Sequence
<220> FEATURE:
<221> NAME/KEY: primer_bind

```
<222> LOCATION: (1)...(20)
<223> OTHER INFORMATION: synthetic oligonucleotide

<400> SEQUENCE: 3
cccatggctc aatctctaat                                                    20

<210> SEQ ID NO 4
<211> LENGTH: 24
<212> TYPE: DNA
<213> ORGANISM: Artificial Sequence
<220> FEATURE:
<221> NAME/KEY: primer_bind
<222> LOCATION: (1)...(24)
<223> OTHER INFORMATION: synthetic oligonucleotide

<400> SEQUENCE: 4
caagcttaaa atgtacgatg agag                                               24

<210> SEQ ID NO 5
<211> LENGTH: 28
<212> TYPE: DNA
<213> ORGANISM: Artificial Sequence
<220> FEATURE:
<221> NAME/KEY: primer_bind
<222> LOCATION: (1)...(28)
<223> OTHER INFORMATION: synthetic oligonucleotide

<400> SEQUENCE: 5
agtgtcgaag aggactaaac ccgaaaat                                           28

<210> SEQ ID NO 6
<211> LENGTH: 1028
<212> TYPE: DNA
<213> ORGANISM: Artificial Sequence
<220> FEATURE:
<221> NAME/KEY: promoter
<222> LOCATION: (1)...(1028)
<223> OTHER INFORMATION: synthetic DNA promoter seqence
<220> FEATURE:
<221> NAME/KEY: misc_feature
<222> LOCATION: (1)...(1028)
<223> OTHER INFORMATION: n = A,T,C or G

<400> SEQUENCE: 6
cttaaaatgt acgatgagag acataaagag aactaataat tgaggagtcc tataatatat        60
aataaagttt attagtaaac ttaattatta aggactccta aaatatatga taggagaaaa       120
tgaatggtga gagatattgg aaaacttaat aattaaggat nttaaaatat atggtaaaag       180
ataggcaaag tatccattat ccccttttaa cttgaagtct acctaggcgc atgtgaaagg       240 ttgattttt gtcacgtcat atagctataa cgtaaaaaaa gaaagtaaaa ttttttaattt       300 tttttaatat atgacatatt ttaaacgaaa tataggacaa aatgtaaatg aatagtaaag       360
gaaacaaaga ttaatactta ctttgtaaga atttaagata aatttaaaat ttaatagatc       420
aactttacgt ctagaaagac ccatatctag aaggaatttc acgaaatcgg cccttattca       480 aaataactt ttaataatg aattttaaat tttagaaat aatatccaat gaataaatga         540
catgtagcat tttacctaaa tatttcaact attttaatcc aatattaatt tgttttattc       600
ccaacaatag aaagtcttgt gcagacattt aatctgactt ttccagtact aaatattaat       660
tttctgaaga ttttcgggtt tagtcctctt cgacactttt ccctctaacc aaagctctta       720
aaactatatt gtgaatgctg attaagttaa acgaaacagt cctaaatctt ttccgtccta       780
tgagaaacaa gattaatcaa ttcacaattt ttttaaaaag aaaaacctgt aagaaattta       840
```

-continued

```
ggcaaacaaa acctaacaca agtttgtttt tgtttttact accaacaaga aattcaaatg      900
gcaaatgtat aacgcatctt agctaattat atgaccagat tcagattaat atacatcttc      960
acccatgcaa tccatttcta tataaagaaa catacacgaa cttgatatta ttagagattg     1020
agccatgg                                                              1028
```

<210> SEQ ID NO 7
<211> LENGTH: 2298
<212> TYPE: DNA
<213> ORGANISM: Artificial Sequence
<220> FEATURE:
<223> OTHER INFORMATION: synthetic hybrid DNA sequence
<220> FEATURE:
<221> NAME/KEY: misc_feature
<222> LOCATION: (1)...(2298)
<223> OTHER INFORMATION: n = A,T,C or G

<400> SEQUENCE: 7

```
aagctttaat tggttgagat tgaacgtaat tcaaattatt ctgagcccaa acccttaaaa       60
ttctaggcgg ttatctttgt ttgaattcat ttttgacatc cctaatgata ttgttcacgt      120
aattaagttt tgtggaagtg agagagtcca attttgataa gaaaagagtc agaaaacgta      180
atattttaaa agtctaaatc tttctacaaa taagagcaaa tttatttatt ttttaatcca      240
ataaatatta atggaggaca aattcaattc acttggttgt aaaataaact taaaccaata      300
accaaaganc taataaatct gaagtggaat tattaaggat aatgtacata gacaatgaag      360
aaataatagg ttcgatgaat taataataat taaggatgtt acaatcatca tgtgccaagt      420
atatacacaa tattctatgg gatttataat ttcgttactt cacttaactt ttgcgtaaat      480
aaaacgaatt atctgatatt ttataataaa acagttaatt aagaaccatc attttttaaca     540 acatagatat attatttcta atagtttaat gatactttta aatcttttaa atttatgtt       600 tcttttagaa aataaaaatt caaaaaaatt aaatatattt acaaaaacta caatcaaaca      660
caacttcata tattaaaagc aaaatatatt ttgaaaattt caagtgtcct aacaaataag     720
acaagaggaa aatgtacgat gagagacata agagaactaa ataattgagg agtcctataa     780 tataataataa agtttattag taaacttaat tattaaggac tcctaaaata tatgatagga    840
gaaaatgaat ggtgagagat attggaaaac ttaataatta aggatnttaa aatatatggt    900
aaaagatagg caaagtatcc attatcccct tttaacttga agtctaccta ggcgcatgtg     960
aaaggttgat ttttttgtcac gtcatatagc tataacgtaa aaaagaaag taaaatttt    1020 aattttttt aatatatgac atattttaaa cgaaatatag gacaaaatgt aaatgaatag    1080 taaggaaac aaagattaat acttactttg taagaattta agataaaatt aaaatttaat    1140
agatcaactt tacgtctaga aagacccata tctagaagga atttcacgaa atcggccctt    1200
attcaaaaat aactttaaa taatgaattt taaaatttaa gaaataatat ccaatgaata     1260
aatgacatgt agcattttac ctaaatattt caactatttt aatccaatat taatttgttt    1320
tattcccaac aatagaaagt cttgtgcaga cattttaatct gacttttcca gtactaaata   1380
ttaattttct gaagattttc gggttttagtc cacaagttt agtgagaagt tttgctcaaa    1440
attttaggtg agaaggttg atatttatct tttgttaaat taatttatct aggtgactat    1500 tatttatta agtagaaatt catatcatta cttttgccaa cttgtagtca taataggagt    1560
aggtgtatat gatgaaggaa taacaagtt cagtgaagtg attaaaataa aatataattt   1620
aggtgtacat caaataaaaa ccttaaagtt tagaaaggca ccgaataatt ttgcatagaa   1680
gatattagta aatttataaa aataaaagaa atgtagttgt caagttgtct tctttttttt   1740
```

-continued

```
ggataaaaat agcagttggc ttatgtcatt cttttacaac ctccatgcca cttgtccaat      1800
tgttgacact taactaatta gtttgattca tgtatgaata ctaaataatt ttttaggact      1860
gactcaaata ttttatatt atcatagtaa tatttatcta atttttagga ccacttatta      1920
ctaaataata aattaactac tactatatta ttgttgtgaa acaacaacgt tttggttgtt      1980
atgatgaaac gtacactata tcagtatgaa aaattcaaaa cgattagtat aaattatatt      2040
gaaaatttga tattttcta ttcttaatca gacgtattgg gtttcatatt ttaaaaaggg      2100
actaaactta gaagagaagt ttgtttgaaa ctacttttgt ctctttcttg ttcccatttc      2160
tctcttagat ttcaaaaagt gaactacttt atctcttctct ttgttcacat tttattttat      2220
tctattataa atatggcatc ctcatattga gattttaga aattattcta atcattcaca      2280
gtgcaaaaga ccatggaa                                                     2298
```

<210> SEQ ID NO 8
<211> LENGTH: 2796
<212> TYPE: DNA
<213> ORGANISM: Solanum esculentum

<400> SEQUENCE: 8

```
gaattctcaa ttgagcccaa ttcaatctcc aatttcaacc cgttttaaaa cttttttatta     60 agatatgttt ctatattgaa agtatgaatt attatctatt taacatcttt taggatttat     120
ctatccattt gctacttttt taacaaaaaa ttcttgagtg aaaattcaaa ttgtgattat     180
aaaagttaaa tatcaatatg ttaaattatt aagattaatc gggtcaaatt ggcgggtcaa     240
ggcccaattc ttttttagcc catttaagct caaagtaaac ttgggtgggt caagacccaa     300
ctcgatttct gttcaaccca ttttaatatt tctattttca acctaacccg ctcatttgat     360 accctacaa atatcatatt tgtgtgtgaa atatttttg ggctggagag agaggccccg       420
aggggagtgg agggggtgggg tggggagaga gagcgagaaa gagtggagag agaaatttga     480
tatgaaatcc tacatatatt acagattgta atgttctaaa ctataacgat ttgtcataaa     540
cacatatcat ggatttgtct ttttgtgtaa ttttcccaat tgtaaatagg acttcgttat     600
ttgaaacttg aaagtgaagt cacatagatt aagtacaaac attaattaaa gaccgtggtg     660
gaatgataaa tatttattta tctttaatta gttattttt tgggagctct ttattccaat     720
gtgagacttt tgcgacatat attcaaattt aatcgaatca caatatgtat tagattgata     780 aaaaataat ttttttacaa tgttagttga gactcataac ttactgccta ttggtaatct     840
atgactccta attccttaat tatttaaata tatcatcttg atcgttaaca aagtaatttc     900
gaaagaccac gagtaagaag acaaacgaga ataccaaaaa attcaaaaat ttaatgtgat     960
ttggtcaatc gatctacgtc cataaaggag atgagtaatc tactataaat atgagagtac    1020
aaaatacaga gagaaacaac ctcaactaat tcactcggaa tacatgagaa gttcacacaa    1080
gtgataacgt atcaaacttg tgacccacac ttttccctct aaccaaagct cttaaaacta    1140
tattgtgaat gctgattaag ttaaacgaaa cagtcctaaa tcttttccgt cctatgagaa    1200
acaagattaa tcaattcaca attttttaa aagaaaaac ctgtaagaaa tttaggcaaa      1260 caaacctaa cacaagtttg tttttgtttt tactaccaac aagaaattca aatggcaaat     1320
gtataacgca tcttagctaa ttatatgacc agattcagat taatatacat cttcacccat    1380
gcaatccatt tctatataaa gaacataca cgaacttgat attattagag attgagcaat     1440
ggagggtaac aacagcagta gcaagtcaac caccaatcca gcattggatc cggatctgga    1500
```

-continued

```
cagcccggat cagccgggtc tggagtttgc ccaatttgct gccggctgct ttttggggagt      1560 cgaattggct ttccagaggg ttggaggagt agtgaagacg gaggttgggt actctcaggg      1620
gaatgtccat gacccgaact acaagcttat ttgctccgga acaaccgaac atgccgaggc      1680
cattcggatc cagtttgacc cgaatgtctg cccgtattcc aatctccttt ctctattttg      1740
gagtcgccat gacccgacca ctctaaatcg ccaggtatca aattcctttg gtgtttcatt      1800
ttatgtgatt aatattaaaa attttttata taaatgtcat gatgatggtt gttgctaggg      1860
taatgatgtg ggaaagcaat accgctcagg aatatattac tataatgatg ctcaggctca      1920
actggcaagg gagtcgttag aagctaagca gaaggaattt atggataaga aaattgtcac      1980
tgaaattctt cctgctaaga gattttatag agctgaagag tatcaccagc aatatctaga      2040
gaagggtggg ggcagaggtt gtaagcagtc ggctgcaaag ggctgcaatg acccaataag      2100
gtgctacggt tgacagcaga tcttttgaatgt tcatagcaac tacaaaagaa cttgttagac      2160
atttgctgtc ttgcttcttt aaatttgaat aaacatgaca atgattctta taactacttg      2220
ctctcttgga tggaataact agttgtcgta aagtattctc ctcttgctaa ttattatctc      2280
tctttatatg gtacctgcaa tttgttgctt tagttacaga ataatggacg tcaattctat      2340
atcttaattt gttttaagtc ttaaatgagg tggtttgtgt ttgaaagcaa tatcaagcat      2400
agtaatacca atgatttagt agatgaactt aatcaaatca aattccaaaa tgcagtctac      2460
aaattgacaa catgaagtta agtgtatctt atgtaaattg acatctttcc tagtagatgc      2520
ctaatacttt tgtaaagact aaaataagca cagatgaggc ttgtgcattt aacttagagt      2580
tcatccttag gtgtggctgc aggagaccct gtagggttgc ttgaagtctt gatggggtag      2640
gagggttgca ttgctatacc acacaaccccc tcttcagcgt caaccttgcg ctgcattcta      2700
atgtatcctt tttctcccca ttcagctccc catgagttct tcacaatcca gtatttggtt      2760
ccatcgacgg ttgtgccata ccccacaata gccaca                                2796
```

<210> SEQ ID NO 9
<211> LENGTH: 363
<212> TYPE: PRT
<213> ORGANISM: Solanum lycopersicum

<400> SEQUENCE: 9

```
Met Glu Ser Pro Arg Val Glu Ser Tyr Asp Lys Met Ser Glu Leu
  1               5                  10                  15

Lys Ala Phe Asp Asp Thr Lys Ala Gly Val Lys Gly Leu Val Asp Ser
                 20                  25                  30

Gly Ile Thr Lys Val Pro Gln Ile Phe Val Leu Pro Pro Lys Asp Arg
             35                  40                  45

Ala Lys Lys Cys Glu Thr His Phe Val Phe Pro Val Ile Asp Leu Gln
         50                  55                  60

Gly Ile Asp Glu Asp Pro Ile Lys His Lys Glu Ile Val Asp Lys Val
     65                  70                  75                  80

Arg Asp Ala Ser Glu Lys Trp Gly Phe Phe Gln Val Val Asn His Gly
                 85                  90                  95

Ile Pro Thr Ser Val Leu Asp Arg Thr Leu Gln Gly Thr Arg Gln Phe
            100                 105                 110

Phe Glu Gln Asp Asn Glu Val Lys Lys Gln Tyr Tyr Thr Arg Asp Thr
        115                 120                 125

Ala Lys Lys Val Val Tyr Thr Ser Asn Leu Asp Leu Tyr Lys Ser Ser
    130                 135                 140
```

```
Val Pro Ala Ala Ser Trp Arg Asp Thr Ile Phe Cys Tyr Met Ala Pro
145                 150                 155                 160

Asn Pro Pro Ser Leu Gln Glu Phe Pro Thr Pro Cys Gly Glu Ser Leu
            165                 170                 175

Ile Asp Phe Ser Lys Asp Val Lys Lys Leu Gly Phe Thr Leu Leu Glu
            180                 185                 190

Leu Leu Ser Glu Gly Leu Gly Leu Asp Arg Ser Tyr Leu Lys Asp Tyr
        195                 200                 205

Met Asp Cys Phe His Leu Phe Cys Ser Cys Asn Tyr Tyr Pro Pro Cys
    210                 215                 220

Pro Gln Pro Glu Leu Thr Met Gly Thr Ile Gln His Thr Asp Ile Gly
225                 230                 235                 240

Phe Val Thr Ile Leu Leu Gln Asp Asp Met Gly Leu Gln Val Leu
                245                 250                 255

His Gln Asn His Trp Val Asp Val Pro Pro Thr Pro Gly Ser Leu Val
            260                 265                 270

Val Asn Ile Gly Asp Phe Leu Gln Leu Leu Ser Asn Asp Lys Tyr Leu
        275                 280                 285

Ser Val Glu His Arg Ala Ile Ser Asn Asn Val Gly Ser Arg Met Ser
    290                 295                 300

Ile Thr Cys Phe Phe Gly Glu Ser Pro Tyr Gln Ser Ser Lys Leu Tyr
305                 310                 315                 320

Gly Pro Ile Thr Glu Leu Leu Ser Glu Asp Asn Pro Pro Lys Tyr Arg
                325                 330                 335

Ala Thr Thr Val Lys Asp His Thr Ser Tyr Leu His Asn Arg Gly Leu
            340                 345                 350

Asp Gly Thr Ser Ala Leu Ser Arg Tyr Lys Ile
        355                 360

<210> SEQ ID NO 10
<211> LENGTH: 196
<212> TYPE: PRT
<213> ORGANISM: Solanum esculentum

<400> SEQUENCE: 10

Met Glu Gly Asn Asn Ser Ser Ser Lys Ser Thr Thr Asn Pro Ala Leu
1               5                   10                  15

Asp Pro Asp Leu Asp Ser Pro Asp Gln Pro Gly Leu Glu Phe Ala Gln
            20                  25                  30

Phe Ala Ala Gly Cys Phe Trp Gly Val Glu Leu Ala Phe Gln Arg Val
            35                  40                  45

Gly Gly Val Val Lys Thr Glu Val Gly Tyr Ser Gln Gly Asn Val His
        50                  55                  60

Asp Pro Asn Tyr Lys Leu Ile Cys Ser Gly Thr Thr Glu His Ala Glu
65                  70                  75                  80

Ala Ile Arg Ile Gln Phe Asp Pro Asn Val Cys Pro Tyr Ser Asn Leu
                85                  90                  95

Leu Ser Leu Phe Trp Ser Arg His Asp Pro Thr Thr Leu Asn Arg Gln
            100                 105                 110

Gly Asn Asp Val Gly Lys Gln Tyr Arg Ser Gly Ile Tyr Tyr Tyr Met
        115                 120                 125

Asp Ala Gln Ala Gln Leu Ala Arg Glu Ser Leu Glu Ala Lys Gln Lys
    130                 135                 140

Glu Phe Met Asp Lys Lys Ile Val Thr Glu Ile Leu Pro Ala Lys Arg
145                 150                 155                 160
```

```
Phe Tyr Arg Ala Glu Glu Tyr His Gln Gln Tyr Leu Glu Lys Gly Gly
            165                 170                 175

Gly Arg Gly Cys Lys Gln Ser Ala Ala Lys Gly Cys Asn Asp Pro Ile
            180                 185                 190

Arg Cys Tyr Gly
        195
```